US012646627B2

(12) United States Patent
Aihara

(10) Patent No.: US 12,646,627 B2
(45) Date of Patent: Jun. 2, 2026

(54) TERMINAL DEVICE, INFORMATION PROCESSING SYSTEM, AND INFORMATION PROCESSING METHOD

(71) Applicant: NEC Corporation, Tokyo (JP)

(72) Inventor: Mana Aihara, Tokyo (JP)

(73) Assignee: NEC CORPORATION, Tokyo (JP)

( * ) Notice: Subject to any disclaimer, the term of this patent is extended or adjusted under 35 U.S.C. 154(b) by 363 days.

(21) Appl. No.: 18/272,866

(22) PCT Filed: Mar. 26, 2021

(86) PCT No.: PCT/JP2021/012865
§ 371 (c)(1),
(2) Date: Jul. 18, 2023

(87) PCT Pub. No.: WO2022/201488
PCT Pub. Date: Sep. 29, 2022

(65) Prior Publication Data
US 2024/0096502 A1 Mar. 21, 2024

(51) Int. Cl.
*G16H 50/80* (2018.01)
*A61B 5/01* (2006.01)
(Continued)

(52) U.S. Cl.
CPC .............. *G16H 50/80* (2018.01); *A61B 5/01* (2013.01); *G06V 20/53* (2022.01); *G06V 40/16* (2022.01)

(58) Field of Classification Search
None
See application file for complete search history.

(56) References Cited

U.S. PATENT DOCUMENTS 10,405,761 B2 * 9/2019 Ouwerkerk .......... A61B 5/7207
2019/0278354 A1 * 9/2019 Alameh .................. G06F 3/013
(Continued)

FOREIGN PATENT DOCUMENTS

| CN | 109473180 A | 3/2019 |
| JP | 2011-223550 A | 11/2011 |

(Continued)

OTHER PUBLICATIONS

Jin, Guanghao, et al. "Crowd recognition based on the fusion of multi-model collaboration." International Conference on Remote Sensing, Mapping, and Image Processing (RSMIP 2024). vol. 13167. SPIE, 2024. (Year: 2024).*

(Continued)

*Primary Examiner* — Michelle M Entezari Hausmann
(74) *Attorney, Agent, or Firm* — Sughrue Mion, PLLC

(57) ABSTRACT

In order to suitably collect information relating to a person who is suspected to have an infectious disease, a terminal device A includes: a communication means communicating with a first terminal device and a second terminal device; a difficulty information obtaining means that obtains information relating to difficulty in obtaining physical condition information in a place around the first terminal device; a selecting means that selects one of the first and second terminal devices based on the information relating to the difficulty in obtaining the physical condition information;

(Continued)

300        10 and a physical condition information obtaining means that obtains, from the terminal device selected by the selecting means, the information relating to the physical condition of the pedestrian.

15 Claims, 14 Drawing Sheets

(51) Int. Cl.
   *G06V 20/52* (2022.01)
   *G06V 40/16* (2022.01)

(56) References Cited

U.S. PATENT DOCUMENTS

| | | | | |
|---|---|---|---|---|
| 2020/0174262 A1* | 6/2020 | Godar | | G06F 3/015 |
| 2021/0409645 A1* | 12/2021 | Xu | | G06V 10/454 |
| 2023/0317285 A1* | 10/2023 | Yadav | | G16H 50/20 |
| | | | | 702/19 |
| 2023/0394822 A1* | 12/2023 | Chou | | G06V 20/41 |

FOREIGN PATENT DOCUMENTS

| | | |
|---|---|---|
| JP | 2012-194808 A | 10/2012 |
| JP | 2013-046668 A | 3/2013 |
| JP | 2017-004165 A | 1/2017 |
| JP | 2019-124502 A | 7/2019 |
| JP | 2019-160015 A | 9/2019 |
| JP | 3228643 U | 11/2020 |

OTHER PUBLICATIONS

Tsitsoulis, Athanasios, and Nikolaos G. Bourbakis. "A methodology for extracting standing human bodies from single images." IEEE transactions on human-machine systems 45.3 (2015): 327-338. (Year: 2015).*

Zhu, Jinguo, et al. "Crowded human detection via an anchor-pair network." Proceedings of the IEEE/CVF Winter Conference on Applications of Computer Vision. 2020. (Year: 2020).*

Alharbey, Riad, et al. "Human Faces Detection and Tracking for Crowd Management in Hajj and Umrah." Computers, Materials & Continua 71.3 (2022). (Year: 2022).*

Prioletti, Antonio, et al. "Part-based pedestrian detection and feature-based tracking for driver assistance: real-time, robust algorithms, and evaluation." IEEE Transactions on Intelligent Transportation Systems 14.3 (2013): 1346-1359. (Year: 2013).*

Pai CJ, Tyan HR, Liang YM, Liao HY, Chen SW. Pedestrian detection and tracking at crossroads. Pattern Recognition. May 1, 2004; 37(5):1025-34. (Year: 2004).*

Lin, Chih-Yang, Hong-Xia Xie, and Hua Zheng. "PedJointNet: Joint head-shoulder and full body deep network for pedestrian detection." IEEE Access 7 (2019): 47687-47697. (Year: 2019).*

International Search Report for PCT Application No. PCT/JP2021/012865, mailed on Jun. 15, 2021.

* cited by examiner

FIG. 1

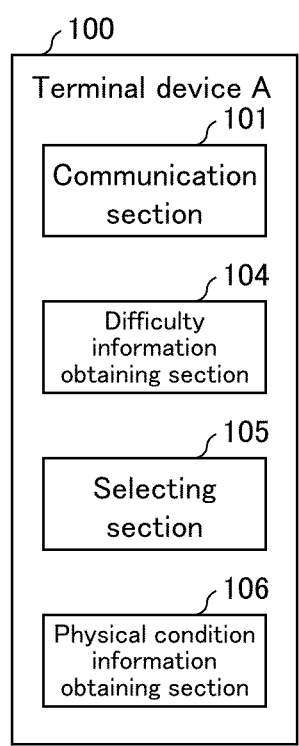

┌ 100

Terminal device A

┌ 101

Communication section

┌ 104

Difficulty information obtaining section

┌ 105

Selecting section

┌ 106

Physical condition information obtaining section

FIG. 2

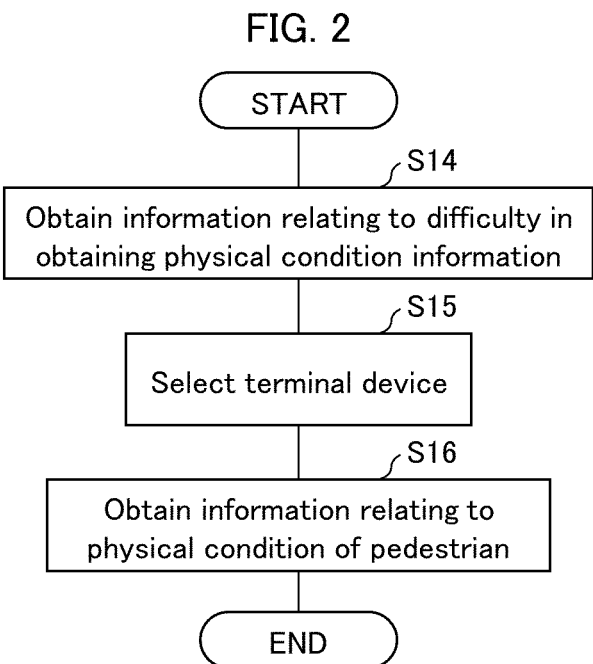

START

S14

Obtain information relating to difficulty in obtaining physical condition information

S15

Select terminal device

S16

Obtain information relating to physical condition of pedestrian

END

Aggregation result

Report

START

S55

S551
Obtain information relating to difficulty in obtaining physical condition information S552
Select terminal device S553
Give instruction to selected terminal device S554
Obtain information relating to physical condition of pedestrian

END

20
Computer

21
Processor

22
Memory

P
Program

30

23

TERMINAL DEVICE, INFORMATION PROCESSING SYSTEM, AND INFORMATION PROCESSING METHOD

This application is a National Stage Entry of PCT/JP2021/012865 filed on Mar. 26, 2021, the contents of all of which are incorporated herein by reference, in their entirety.

TECHNICAL FIELD

The present invention relates to a terminal device, an information processing system, and an information processing method each of which collects information relating to a person who is suspected to have an infectious disease.

BACKGROUND ART

In recent years, due to the effect of COVID-19 spread around the world, infectious disease control measures have been taken in areas having heavy traffic of people. For example, in airports and the like, a fixed thermometry system is set. In slum areas and the like where control of infectious disease patients is difficult and infectious disease patients tend to increase, monitoring of people and a verification test of measured body temperatures are conducted with use of a drone. As techniques relating to this, there are the inventions disclosed in Patent Literatures 1 and 2 below.

Patent Literature 1 relates to an infection spread prevention aid device that aids prevention of spread of an infectious disease, an operation method and an operation program of the device, and an infection spread prevention aid system. The infection spread prevention aid device includes: an infection determination section that determines, on the basis of biological information or biological information history, whether or not subjects to be monitored are infected with an infectious disease; and a contribution information presenting section that presents contribution information in a case where subjects to be monitored include a person who has been determined, by the infection determination section, to be infected with an infectious disease, the contribution information being given on the basis of the history of movement of two or more persons, the contribution information contributing to prevention of spread of an infectious disease.

Patent Literature 2 relates to an infection notification method and an infection notification device. According to the infection notification method, in a case where a user is determined to be infected with a disease, an identifier of a terminal device which has carried out wireless communication with a terminal device of the infected person for a designated period or more in a predetermined period within a designated distance is specified on the basis of (i) the identifier of the terminal device of the infected person and the predetermined period and (ii) contact information stored in a storage section. Then, according to this method, the terminal device having the specified identifier is notified of the infection information.

CITATION LIST

Patent Literature

Patent Literature 1

Japanese Patent Application Publication, Tokukai, No. 2017-004165

Patent Literature 2

Japanese Patent Application Publication, Tokukai, No. 2012-194808

SUMMARY OF INVENTION

Technical Problem

The invention disclosed in Patent Literature 1 (i) collects biological information and movement history of hospitalized patients chosen as subjects to be monitored and (ii) presents information contributing to determination of infection with an infectious disease and to prevention of spread of the infectious disease. However, in a case where the spread of an infectious disease is expected not only in a hospital but also in a larger area, it is difficult to designate the subjects to be monitored.

Therefore, it is desired that a device detecting a person who is suspected to have an infectious disease be set at a location where the device can obtain information of many people. However, in order to set the device, a sufficient space is required. Further, if the field of vision becomes poor due to, e.g., installation of a special facility and/or the crowd of people in an event, it is sometimes difficult to obtain the information with the device.

Patent Literature 2 discloses the infection notification method involving use of the terminal device. However, in a case where the terminal device is used to collect the information, collection of the information is difficult in a place where many obstacles shielding electric waves are present. Particularly for communication, such as 5G, vulnerable to a blocking object, this problem is notable.

An example aspect of the present invention was made in view of the above problems, and an example object of the present invention is to provide a technique that suitably collects, according to a situation such as a situation of an obstacle, information relating to a person who is suspected to have an infectious disease in a given area.

Solution to Problem

A terminal device in accordance with an example aspect of the present invention includes at least one processor, the at least one processor executing: a process of communicating with a first terminal device including a detecting section that detects information relating to a physical condition of a pedestrian and with a second terminal device including an obtaining section that obtains information relating to a physical condition of the pedestrian from a mobile terminal of the pedestrian; a process of obtaining information relating to difficulty in obtaining physical condition information in a place around the first terminal device; a process of selecting one of the first terminal device and the second terminal device on a basis of the information relating to the difficulty in obtaining the physical condition information; and a process of obtaining, from the one of the first and second terminal devices thus selected, the information relating to the physical condition of the pedestrian.

An information processing system in accordance with an example aspect of the present invention includes at least one processor, the at least one processor executing: a process of communicating with a first terminal device including a detecting section that detects information relating to a physical condition of a pedestrian and with a second terminal device including an obtaining section that obtains information relating to a physical condition of the pedestrian from a mobile terminal of the pedestrian; a process of obtaining information relating to difficulty in obtaining physical condition information in a place around the first terminal device; a process of selecting one of the first terminal device and the second terminal device on a basis of the information relating to the difficulty in obtaining the physical condition information; and a process of obtaining, from the one of the first and second terminal devices thus selected, the information relating to the physical condition of the pedestrian.

An information processing method including: obtaining information relating to difficulty in obtaining physical condition information in a place around a first terminal device including a detecting section that detects information relating to a physical condition of a pedestrian; selecting, on a basis of the information relating to the difficulty in obtaining the physical condition information, one of the first terminal device and a second terminal device including an obtaining section that obtains information relating to a physical condition of the pedestrian from a mobile terminal of the pedestrian; and obtaining, from the one of the first and second terminal devices thus selected, the information relating to the physical condition of the pedestrian.

Advantageous Effects of Invention

With an example aspect of the present invention, information relating to a person who is suspected to have an infectious disease in a given area can be collected suitably according to a situation such as a situation of an obstacle.

BRIEF DESCRIPTION OF DRAWINGS

FIG. 1 is a block diagram illustrating a functional configuration of a terminal device A in accordance with a first example embodiment of the present invention.

FIG. 2 is a flowchart illustrating a flow of an information processing method in accordance with the first example embodiment of the present invention.

DESCRIPTION OF EMBODIMENTS

Background of the Present Invention

Figure 3:
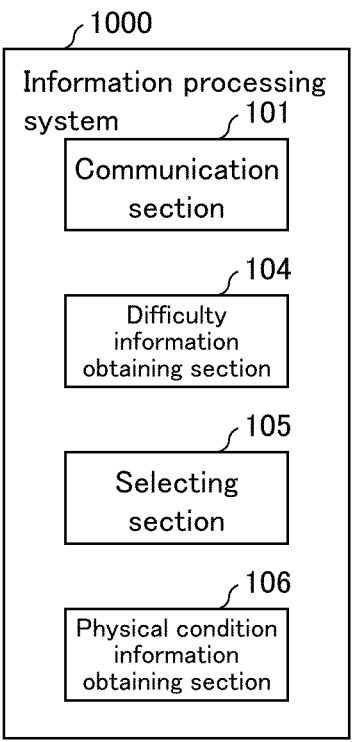
FIG. 3 is a block diagram illustrating a functional configuration of an information processing system in accordance with the first example embodiment of the present invention.

Due to the effect of COVID-19 spread around the world in 2020, many people around the world infected with an infectious diseases, resulted in death of many people. The world economic activity was forced to suspend by the increase in the number of people infected with infectious diseases, which gave a serious impact on various aspects. Particularly, in metropolitan areas and countries where many tourists visited for traveling (e.g., Hawaii, Ney York in the United Stated), the number of people infected with an infectious disease increased. Consequently, these areas stopped accepting tourists. This worsened the economic situation of people who engaged in the tourist industry, and consequently security deteriorated in the metropolitan areas.

Some countries such as Brazil, Thailand, and Kenya involved vulnerability in control of the sanitary environment of poor people in slum areas. Thus, particularly in these countries, the number of people infected with an infectious disease increased to a level that made the governments to take nation-wide measures. However, it was difficult to investigate the infectious disease in a limited space. Not only that, many local citizens were complaint about staff members sent from the government. Various tests involving use of drones were also conducted. However, the drones are required to emit sounds while flying, and thus there was a possibility that the local citizens may be complaint of noise troubles.

Now, entering the New Normal era, technical measures are also required in order to construct an environment that can find, at an early stage, a person who is suspected to have an infectious disease while maintaining economic activities. The measures against infectious diseases are essential particularly in metropolitan areas including slum areas and tourist spots, where quite a number of people got an infectious disease. However, while crowded areas such as metropolitan areas including slums and tourist spots have a complicated lot layout, most conventionally-proposed techniques assume use in a space in which a communication environment is considered, such as an interior space. Thus, no technique applicable to an outdoor space or to a complicated narrow space has been proposed.

It is required to construct a flexible technical environment that can deal with any kinds of space and to propose a measure that also considers the viewpoint of a subject are required.

First Example Embodiment

The following description will discuss an example embodiment of the present invention with reference to the drawings. The present example embodiment is a basic form of example embodiments described later.
(Configuration of Terminal Device A)

The following will describe, with reference to FIG. 1, a configuration of a terminal device A100 in accordance with the present example embodiment. FIG. 1 is a block diagram illustrating a functional configuration of the terminal device A100 in accordance with a first example embodiment of the present invention. As shown in FIG. 1, the terminal device A100 includes a communication section 101, a difficulty information obtaining section 104, a selecting section 105, and a physical condition information obtaining section 106.

The communication section 101 communicates with a terminal device B, which is different from the terminal device A, and with a terminal device C, which is different from the terminal devices A and B. The terminal device B may also be called a "first terminal device", and the terminal device C may also be called a "second terminal device".

The terminal device B includes a detecting means that detects information relating to a physical condition of a pedestrian. The terminal device C includes an obtaining means that obtains, from a mobile terminal of a pedestrian, information relating to a physical condition of the pedestrian.

The difficulty information obtaining section 104 obtains information relating to the difficulty in obtaining the physical condition information in a place around the terminal device B.

Here, the "information relating to the difficulty in obtaining the physical condition information in the place around the terminal device B" refers to information indicating the degree of ease of the terminal device B obtaining physical condition information of a pedestrian or the like. In an example, the information relating to the difficulty can be obtained from the result of detection carried out by at least one of the detecting means and other means included in the terminal device B. For example, the following situation is assumed. That is, there are so many pedestrians and obstacles that images which can be biometrically authenticated cannot be obtained and consequently some people cannot be biometrically authenticated. In such a case, the information relating to the difficulty can be expressed by a difference or a ratio between:

a total number of living bodies recognized, through biometric authentication, by the detecting means included in the terminal device B in a predetermined period; and a total number of faces recognized by the detecting means or another means included in the terminal device B in the predetermined period.

Here, a specific example of the predetermined period may be approximately one minute to approximately an hour. This, however, by no means limits the present example embodiment. In other words, the information relating to the difficulty in obtaining the physical condition information in the place around the terminal device B is information that can be updated in real time in a cycles of the predetermined period.

Thus, in an example, the difficulty information obtaining section 104 can obtain information that indicates, in real time, the difficulty in obtaining the physical condition information in the place around the terminal device B.

Used as the information relating to the difficulty may be information relating to a status of communication between a mobile terminal of a user and the terminal device C. In the present example embodiment, there is no limitation on specific arrangement of the terminal devices B and C. For example, in a case where the terminal devices B and C are arranged mixedly, information relating to the status of communication between the mobile terminal of the user and the terminal device C may be suitably used as the information relating to the difficulty.

The information relating to the communication status is also information that can be updated in real time. Thus, also with this configuration, the difficulty information obtaining section 104 can obtain information that indicates, in real time, the difficulty in obtaining the physical condition information in the place around the terminal device B.

On the basis of the information relating to the difficulty in obtaining the physical condition information obtained by the difficulty information obtaining section 104, the selecting section 105 selects one of the terminal devices B and C. Here, a specific example of the selecting process carried out by the selecting section 105 may be as follows. That is, in a case where the information relating to the difficulty in obtaining the physical condition information indicates that the degree of difficulty in obtaining the physical condition information is higher than a given degree, the selecting section 105 selects the terminal device C. This, however, by no means limits the present example embodiment. Further, in a case where the information relating to the difficulty in obtaining the physical condition information indicates that the degree of difficulty in obtaining the physical condition information is not higher than the given degree, the selecting section 105 may select the terminal device B.

Specifically, in a case where a total number of recognized faces and a total number of living bodies are used as the information relating to the difficulty in obtaining the physical condition information, it may be determined that obtaining of the physical condition information is difficult if a difference between the total number of recognized faces and the total number of living bodies is not less than a given value (for example, 10) or if a ratio between the total number of recognized faces and the total number of living bodies is not more than a given value (for example, 0.5).

Further, in a case where the information relating to the status of communication between the mobile terminal of the user and the terminal device C is used as the information relating to the difficulty in obtaining the physical condition information, it may be determined that obtaining of the physical condition is difficult if a retransmission rate is not less than a given value (for example, 50%).

The physical condition information obtaining section 106 obtains, from the terminal device selected by the selecting section 105, the information relating to the physical condition of the pedestrian.

Note that the physical condition information obtaining section 106 may be configured to function as an instruction section that instructs the terminal device selected by the selecting section 105 to obtain the information relating to the physical condition of the pedestrian. In the case of this configuration, the terminal device selected by the selecting section 105 may be configured to obtain, in response to reception of the instruction, the information relating to the physical condition of the pedestrian.

(Effects of Terminal Device A)

As discussed above, the terminal device A100 in accordance with the present example embodiment includes:

the communication section 101 that communicates with the terminal device B (first terminal device) including the detecting means that detects information relating to a physical condition of a pedestrian and with the terminal device C (second terminal device) including the obtaining means that obtains information relating to a physical condition of the pedestrian from a mobile terminal of the pedestrian;

the difficulty information obtaining section 104 that obtains information relating to the difficulty in obtaining the physical condition information in a place around the terminal device B;

the selecting section 105 that selects one of the terminal devices B and C on the basis of the information relating to the difficulty in obtaining the physical condition information; and the physical condition information obtaining section 106 that obtains, from the terminal device selected by the selecting section 105, the information relating to the physical condition of the pedestrian.

The terminal device A100 configured as above refers to the information relating to the difficulty in obtaining the physical condition information in the place around the terminal device B, and selects one of the terminal devices B and C; then, the terminal device A100 obtains the information relating to the physical condition of the pedestrian from the selected terminal device. This makes it possible to provide an effect of suitably collecting the information relating to the physical condition of the pedestrian in accordance with the difficulty in obtaining the physical condition information.

For example, it is possible to suitably collect information relating to a physical condition of a user via a terminal device even in a place including the crowd of people or a town including many narrow alleys.

<Flow of Information Processing Method>

Subsequently, the following will describe, with reference to FIG. 2, an information processing method in accordance with the first example embodiment. FIG. 2 is a flowchart illustrating a flow of the information processing method in accordance with the first example embodiment of the present invention.

(Step S14)

First, in step S14, the difficulty information obtaining section 104 of the terminal device A100 obtains information relating to the difficulty in obtaining physical condition information in a place around the terminal device B (first terminal device) including the detecting means that detects information relating to a physical condition of a pedestrian. The "information relating to the difficulty in obtaining the physical condition information" has been discussed above, and therefore a description thereof will be omitted here.

(Step S15)

Subsequently, in step S15, the selecting section 105 of the terminal device A100 selects, on the basis of the information relating to the difficulty in obtaining the physical condition information obtained in step 1S4, one of the terminal device B and the terminal device C (second terminal device) including the obtaining means that obtains information relating to a physical condition of the pedestrian from a mobile terminal of the pedestrian. The selecting process carried out by the selecting section 105 is identical to that discussed above.

(Step S16)

Then, in step S16, the physical condition information obtaining section 106 of the terminal device A100 obtains the information relating to the physical condition of the pedestrian from the terminal device selected in step S15.

(Effects of Information Processing Method)

With the information processing method configured as above, it is possible to attain similar effects to those given by the terminal device A100 in accordance with the present example embodiment.

(Information Processing System)

Subsequently, the following will describe, with reference to FIG. 3, an information processing system in accordance with the first example embodiment. FIG. 3 is a block diagram illustrating a configuration of an information processing system 1000 in accordance with the present example embodiment. As shown in FIG. 3, the information processing system 1000 in accordance with the present example embodiment includes constituent elements similar to those of the terminal device A100 in accordance with the present example embodiment. Note that, in the information processing system 1000, the communication section 101, the difficulty information obtaining section 104, the selecting section 105, and the physical condition information obtaining section 106 in the information processing system 1000 may not be disposed inside a single terminal device, unlike the terminal device A100. For example, in the information processing system 1000, the communication section 101, the difficulty information obtaining section 104, the selecting section 105, and the physical condition information obtaining section 106 disposed in respective different devices may be arranged dispersedly over a global network or a local network. For example, the communication section 101, the difficulty information obtaining section 104, the selecting section 105, and the physical condition information obtaining section 106 disposed in respective different devices may be connected with each other through wired or wireless communication so as to be communicable with each other. Examples of the wireless communication include WiFi (registered trademark), LTE, 4G, 5G, and local 5G.

(Effects of Information Processing System)

With the information processing system 1000 configured as above, it is possible to attain similar effects to those given by the terminal device A100 in accordance with the present example embodiment.

Second Example Embodiment

The following description will discuss a second example embodiment of the present invention in detail with reference to the drawings. Note that members having identical functions to those of the first example embodiment are given identical reference signs, and a description thereof will be omitted.

(Configuration of Mobile Terminal)

Figure 4:
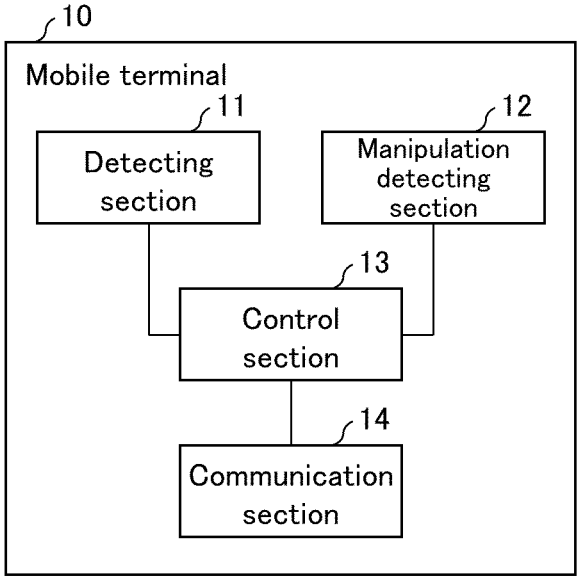
FIG. 4 is a block diagram illustrating a functional configuration of a mobile terminal in accordance with a second example embodiment of the present invention.

The following will describe, with reference to FIG. 4, a configuration of a mobile terminal 10 in accordance with the present example embodiment. FIG. 4 is a block diagram illustrating a functional configuration of the mobile terminal in accordance with the first example embodiment of the present invention. The mobile terminal 10 includes a detecting section 11, a manipulation detecting section 12, a control section 13, and a communication section 14.

The detecting section 11 has a thermography function, and detects a body temperature of a user of the mobile terminal 10, the user being a subject to be monitored.

The manipulation detecting section 12 detects, for example, an event occurring as a result of touching on a touch panel, which is a display device of the mobile terminal 10, thereby detecting that the mobile terminal 10 has been manipulated. In response to manipulation on the terminal device 10 (mobile terminal), the control section 13 carries out the following process.

Note that the manipulation on the terminal device 10 may be manipulation on a hardware button of the terminal device or manipulation on Graphical User Interface (GUI) displayed by the display section of the terminal device 10. The hardware button is, for example, a home button that is to be pressed for unlocking.

When the manipulation detecting section 12 detects manipulation on the mobile terminal 10, the control section 13 obtains body temperature information of the user from the detecting section 11. Further, the control section 13 obtains at least one of information relating to the user and information relating to the mobile terminal 10. The information relating to the user is, for example, a result of authentication of user's face captured by a camera. The information relating to the mobile terminal 10 is, for example, a Media Access Control (MAC) address of the mobile terminal 10. These pieces of information are used as information for specifying the user of the mobile terminal 10. However, since the user is not necessarily an owner of the mobile terminal 10. Thus, it is more preferable to specify the user by, e.g., face recognition.

Note that the above-discussed example of the process of the control section 13 by no means limits the present example embodiment. For example, instead of the configuration in which the control section 13 carries out the process in response to manipulation on the mobile terminal 10 by the manipulation detecting section 12, the control section 13 may obtain the body temperature information of the user from the detecting section 11 at certain time intervals (for example, at time intervals of 3 to 4 hours).

Further, in a case where the control section 13 receives an instruction from the terminal device A, the control section 13 may obtain, in response to reception of the instruction, the body temperature information of the user from the detecting section 11.

The communication section 14 is constituted by a device having a near field communication function such as a beacon, Small Cell, local 5G, or local Long Term Evolution (LTE). The control section 13 transmits (i) the body temperature information of the user and (ii) at least one of the information relating to the user and the information relating to the mobile terminal 10 to the later-described terminal device C via the communication section 14. Note that the communication section 14 is not limited to the near field communication, and may alternatively be communication that uses a public network working over a base station. Note that the body temperature information of the user is used to determine whether or not the user is suspected to have an infectious disease. For example, if the body temperature is not less than a given value, the terminal device 10 determines that the user is a person who is suspected to have an infectious disease.

Since the communication section 14 transmits information to the terminal device C through near field communication, the terminal device C can collect information relating to a person who is suspected to have an infectious disease even if there is an obstacle in a place around the terminal device C.

As discussed above, the mobile terminal 10 in accordance with the present example embodiment is configured such that, in response to the manipulation on the mobile terminal 10, the control section 13 transmits (i) the information indicating the body temperature of the user detected by the detecting section 11 and (ii) at least one of the information relating to the user and the information relating to the mobile terminal 10 to the terminal device via the communication section 14. Thus, with the terminal device, it is possible to easily collect the information relating to the person who is suspected to have an infectious disease.

(Flow of Information Transmitting Method)

Figure 5:
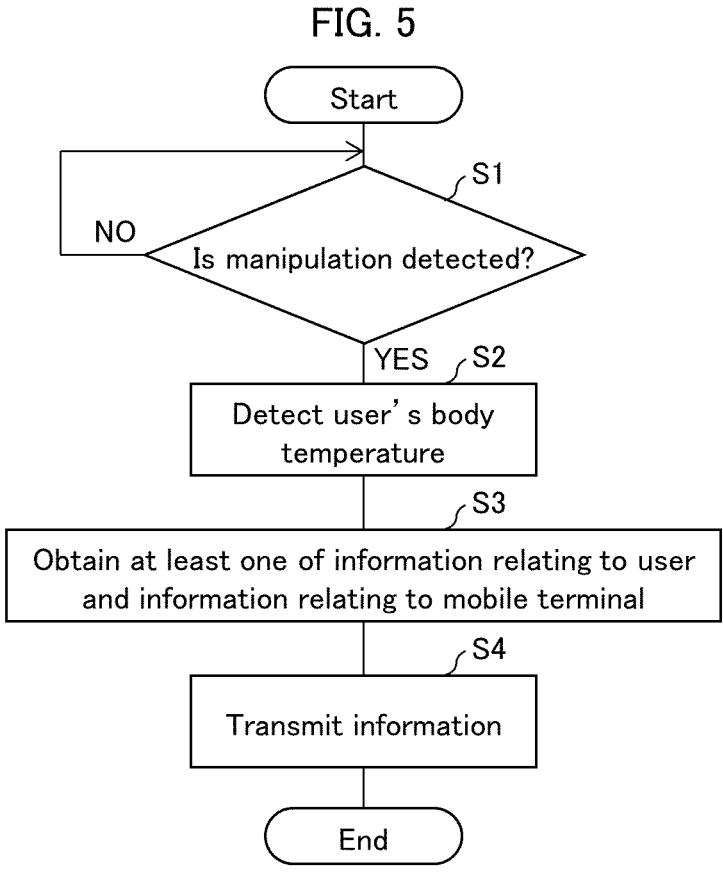
FIG. 5 is a flowchart illustrating a flow of an information processing method carried out by the mobile terminal in accordance with the second example embodiment of the present invention.

FIG. 5 is a flowchart illustrating a flow of an information transmitting method carried out by the mobile terminal 10 in accordance with the first example embodiment of the present invention. First, the control section 13 determines, via the manipulation detecting section 12, whether or not the mobile terminal 10 is manipulated (S1). If it is determined that the mobile terminal 10 is not manipulated (S1, No), the process in step S1 is carried out again.

Meanwhile, if it is determined that the mobile terminal 10 is manipulated (S1, Yes), the control section 13 detects, via the detecting section 11, a body temperature of a user (S2). Then, the control section 13 obtains at least one of information relating to the user and information relating to the mobile terminal 10 (S3). Then, the control section 13 transmits (i) the information indicating the body temperature of the user and (ii) at least one of the information relating to the user and the information relating to the mobile terminal 10 to the later-described terminal device C via the communication section 14 (S4).

As discussed above, the information transmitting method in accordance with the present example embodiment detects, in response to the manipulation on the mobile terminal 10, the body temperature of the user and transmits (i) the information indicating the body temperature of the user thus detected and (ii) at least one of the information relating to the user and the information relating to the mobile terminal 10 to the terminal device. Thus, with the terminal device, it is possible to easily collect the information relating to the person who is suspected to have an infectious disease.

Third Example Embodiment (Configuration of Terminal Device B)

Figure 6:
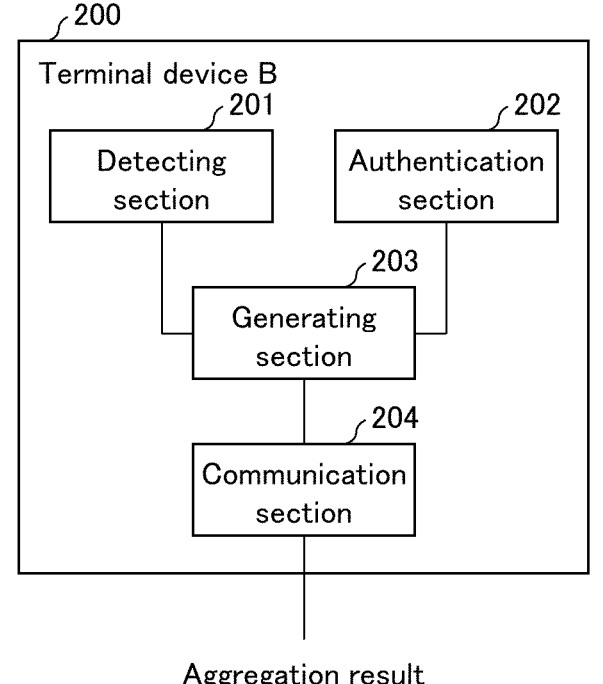
FIG. 6 is a block diagram illustrating a functional configuration of a terminal device B in accordance with a third example embodiment of the present invention.

The following will describe, with reference to FIG. 6, a configuration of a terminal device B200 in accordance with the present example embodiment. FIG. 6 is a block diagram illustrating a functional configuration of the terminal device B200 in accordance with a third example embodiment of the present invention. The terminal device B200 includes a detecting section 201, an authentication section 202, a generating section 203, and a communication section 204.

The detecting section 201 (detecting means) has a thermography function, and detects a body temperature of a pedestrian who is a subject to be monitored in a detectable range.

The detecting section 201 may be configured as follows. That is, after detecting the body temperature, the detecting section 201 supplies, to the authentication section 202, the body temperature and information indicating a position, an image, and/or the like of the pedestrian whose body temperature has been detected, in such a manner that the body temperature and the information is associated with each other.

The authentication section 202 obtains an image of the pedestrian's face captured by a camera or the like. Here, the image of the pedestrian's face obtained by the authentication section 202 may be a still image or a moving image.

Then, the authentication section 202 analyzes the image of the face to recognize a coughing motion, a sneezing motion, and/or the like, and detects a symptom which is suspected to be of an infectious disease. Further, in order to prevent duplication of the analysis of the same pedestrian, the authentication section 202 may be configured as follows. That is, the authentication section 202 stores the image of the pedestrian's face together with a face ID. Then, before analyzing the image of the pedestrian's face, the authentication section 202 authenticates the image of the pedestrian's face with respect to images of faces stored therein. If the pedestrian is identical to a pedestrian who has been already analyzed, the authentication section 202 does not analyze the face of the pedestrian. However, it may happen that the pedestrian identical to a pedestrian who has been already analyzed does not cough or sneeze at or near the terminal device B200 at the moment. Thus, even if the pedestrian is identical to a person who has been already analyzed, the authentication section 202 may carry out analysis of the pedestrian every time he/she passes by the terminal device B200. Alternatively, even if a pedestrian is identical to a person who has been already analyzed, the authentication section 202 may carry out analysis of the pedestrian after a predetermined period of time (e.g., 3 to 4 hours) since he/she has passed the place.

On the basis of the body temperature information detected by the detecting section 201 and the symptom suspected to be of an infectious disease detected by the authentication section 202, the generating section 203 comprehensively determines whether or not the pedestrian is suspected to have an infectious disease, generates information given by aggregation of the determination results, and outputs the generated information to the communication section 204. For example, the information given by the aggregation includes the total number of detected pedestrians, the number of pedestrians determined to be suspected to have an infectious disease, and the symptom suspected to be of an infectious disease, for example.

In the above process, the generating section 203 can associate the information indicating the body temperature of the pedestrian detected by the detecting section 201 with the symptom detected by the authentication section 202. For example, the face ID given by the authentication section 202 may be assigned to the information indicating the body temperature of the pedestrian detected by the detecting section 201 and the symptom detected by the authentication section 202.

The generating section 203 may incorporate, into the information given by aggregation, the "information relating to the difficulty in obtaining the physical condition information in the place around the terminal device B".

Here, the information relating to the difficulty is information indicating the degree of ease of the terminal device B200 obtaining the physical condition information. For example, the information relating to the difficulty can be obtained from a detection result given by the detecting section 201 included in the terminal device B200. For example, the information relating to the difficulty can be expressed by a difference between:

a total number of living bodies that the detecting section 201 recognizes through biometric authentication in a predetermined period; and a total number of faces recognized by the detecting section 201 in the predetermined period.

Here, a specific example of the predetermined period may be approximately one minute to approximately an hour. This, however, by no means limits the present example embodiment. In other words, the information relating to the difficulty in obtaining the physical condition information in the place around the terminal device B200 is information that can be updated in real time in a cycles of the predetermined period.

The communication section 204 communicates with the terminal device A100 through a communication network such as LAN. The communication section 204 transmits, to the terminal device A100, the aggregation result generated by the generating section 203. Note that the communication section 204 may carry out communication through a wired or wireless network. The communication section 204 may be configured to serve as a base station of wireless communication such as LTE, 4G, or 5G. Alternatively, the communication section 204 may be configured to be capable of carrying out communication via a base station of wireless communication such as LTE, 4G, or 5G.

Further, the communication section 204 may be configured to serve also as an obtaining section that obtains an instruction from the terminal device A100. For example, the communication section 204 may be configured to be capable of receiving an instruction to obtain information relating to a physical condition of a pedestrian. In the case of this configuration, for example, if the communication section 204 receives, from the terminal device A100, the instruction to obtain the information relating to the physical condition of the pedestrian, the detecting section 201, the authentication section 202, the generating section 203, and the communication section 204 may carry out the above-discussed process in response to reception of the instruction.

As discussed above, the terminal device B200 in accordance with the present example embodiment is configured such that: the generating section 203 generates information given by aggregation of the information indicating the body temperature of the pedestrian detected by the detecting section 201 and the symptom suspected to be of an infectious disease detected by the authentication section 202; and the communication section 204 transmits, to the terminal device A100, the information generated by the generating section 203. Thus, the terminal device A100 can obtain the result of the aggregation of the results from a plurality of terminal devices B200. That is, the terminal device A100 can collect information in the entire area where the terminal devices B200 are provided.

Further, as discussed above, the terminal device B200 in accordance with the present example embodiment may be configured such that, if the communication section 204 receives, from the terminal device A100, an instruction to obtain information relating to a physical condition of a pedestrian, the detecting section 201, the authentication section 202, the generating section 203, and the communication section 204 carry out the above-discussed process in response to reception of the instruction. Thus, the terminal device B200 in accordance with the present example embodiment makes it possible to suitably obtain the information relating to the physical condition of the pedestrian on the basis of the instruction from the terminal device A100.

(Flow of Information Transmitting Method)

Figure 7:
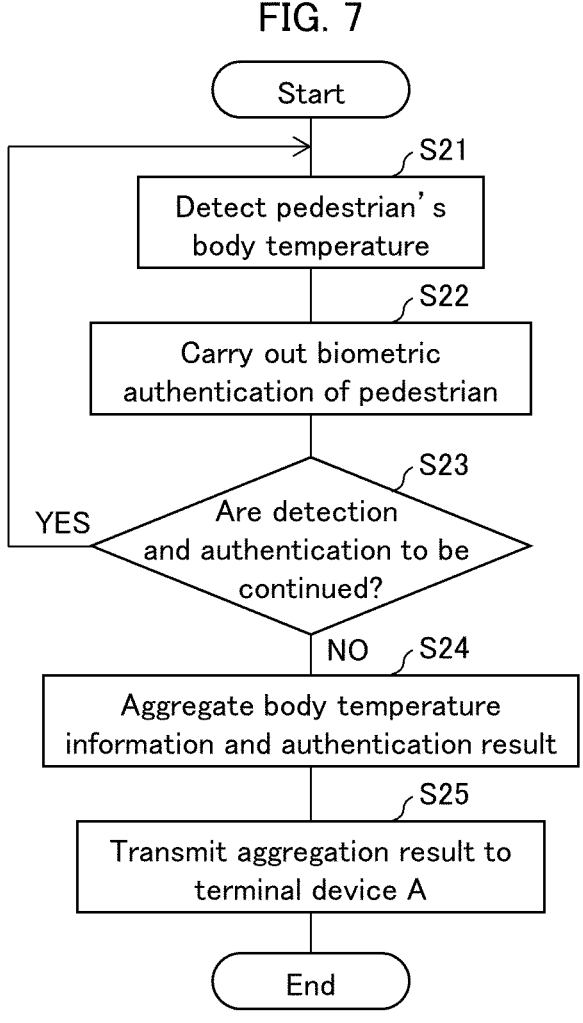
FIG. 7 is a flowchart illustrating a flow of an information processing method carried out by the mobile terminal B in accordance with the third example embodiment of the present invention.

FIG. 7 is a flowchart illustrating a flow of an information processing method carried out by the terminal device B200 in accordance with the third example embodiment of the present invention. First, the detecting section 201 detects a body temperature of a pedestrian (S21). Then, the authentication section 202 carries out biometric authentication of the pedestrian (S22).

Next, the generating section 203 determines whether to continue the body temperature detection by the detecting section 201 and the biometric authentication by the authentication section 202 (S23). If it is determined that the detection and authentication are to be continued (S23, Yes), the process returns to step S21 and the process of step S21 and its subsequent processes are carried out again.

If it is determined that the detection and authentication are not to be continued (S23, No), the generating section 203 aggregates the body temperature information and the authentication result (S24). Then, the communication section 204 transmits, to the terminal device A100, the aggregation result generated by the generating section 203 (S25).

Note that the above-discussed information transmitting method may be configured as follows. That is, in step S21, the communication section 204 determines whether or not the communication section 204 has received, from the terminal device A100, an instruction to obtain information relating to a physical condition of a pedestrian; then, if the communication section 204 determines that the instruction has been received, detection of the body temperature of the pedestrian is carried out and then the process advances to step S22 and its subsequent steps.

The detection in step S21, the authentication in step S22, and the aggregation of the results in step S24 may be carried out in parallel. Further, even while the detection in step S21 and the authentication in step S22 are continued, the aggregation of the results may be carried out periodically.

As discussed above, the information transmitting method in accordance with the present example embodiment generates the information given by aggregation of the information indicating the detected body temperature of the pedestrian and the detected symptom suspected to be of an infectious disease, and transmits the generated information to the terminal device A100. Thus, the terminal device A100 can obtain the result of the aggregation of the results from a plurality of terminal devices B200. That is, the terminal device A100 can collect information in the entire area where the terminal devices B200 are provided.

The information transmitting method in accordance with the present example embodiment may execute the steps in response to reception of an instruction to obtain information relating to a physical condition of a pedestrian, the instruction being from the terminal device A100. Consequently, with the information transmitting method in accordance with the present example embodiment, it is possible to suitably obtain the information relating to the physical condition of the pedestrian in accordance with the instruction from the terminal device A100.

Fourth Example Embodiment (Configuration of Terminal Device C)

Figure 8:
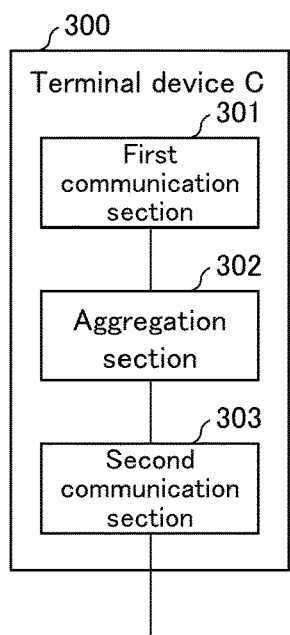
FIG. 8 is a block diagram illustrating a functional configuration of a terminal device C in accordance with a fourth example embodiment of the present invention.

The following will describe, with reference to FIG. 8, a configuration of a terminal device C300 in accordance with the present example embodiment. FIG. 8 is a block diagram illustrating a functional configuration of the terminal device C300 in accordance with a fourth example embodiment of the present invention. The terminal device C300 includes a first communication section 301, an aggregation section 302, and a second communication section 303.

The first communication section 301 is constituted by a device having a near field communication function such as a beacon, Small Cell, local 5G, or local LTE. The first communication section 301 can be set in a narrow space. The first communication section 301 receives, from the mobile terminal 10, (i) body temperature information of a user and (ii) at least one of information relating to the user and information relating to the mobile terminal 10.

The aggregation section 302 aggregates information received via the first communication section 301. For example, in a case where information from a user of the same mobile terminal 10 is received two or more times, aggregation is carried out such that only the information obtained one time is left and the other information is removed. The information given by the aggregation includes a total number of users of mobile terminals 10 from which the information was received, the number of users determined to be suspected to have an infectious disease, and a symptom suspected to be of an infectious disease, for example.

Note that, in a case where the aggregation section 302 has received information from a user of the same mobile terminal 10 two or more times in a certain period of time, the aggregation section 302 may carry out aggregation such that only the information obtained one time is left and the other information is removed.

The aggregation section 302 may incorporate, into the information given by the aggregation, the "information relating to difficulty in obtaining physical condition information in the place around the terminal device B".

Here, the information relating to the difficulty in obtaining the physical condition information is information indicating the degree of ease of the terminal device B200 obtaining the physical condition information.

The aggregation section 302 may incorporate, as the information relating to the difficulty in obtaining the physical condition information, information relating to a status of communication between the mobile terminal of the user and the terminal device C300 into the information given by the aggregation. In the present example embodiment, there is no limitation on specific arrangement of the terminal devices B200 and C300. For example, in a case where the terminal devices B200 and C300 are arranged mixedly, information relating to a status of communication between the mobile terminal of the user and the terminal device C may be suitably used as the information relating to the difficulty.

The second communication section 303 communicates with the terminal device A100 through a local network such as LAN. The second communication section 303 transmits, to the terminal device A100, the aggregation result given by aggregation carried out by the aggregation section 302. Note that the second communication section 303 may carry out communication through a wired or wireless network.

Further, the first communication section 301 may be configured to serve also as an obtaining section that obtains an instruction from the terminal device A100. For example, the first communication section 301 may be configured to be capable of receiving an instruction to obtain information relating to a physical condition of a pedestrian. In the case of this configuration, for example, if the first communication section 301 receives, from the terminal device A100, the instruction to obtain the information relating to the physical condition of the pedestrian, the first communication section 301 may obtain the physical condition information of the user in response to reception of the instruction. Further, the aggregation section 302 and the second communication section 303 may also carry out the above-discussed process in response to reception of the instruction.

Each of the first communication section 302 and the second communication section 303 may be configured to serve as a base station of wireless communication such as LTE, 4G, or 5G. Alternatively, each of the first communication section 302 and the second communication section 303 may be configured to be capable of carrying out communication via a base station of wireless communication such as LTE, 4G, or 5G.

As discussed above, the terminal device C300 in accordance with the present example embodiment is configured such that the aggregation section 302 aggregates information received via the first communication section 301. Then, the second communication section 303 transmits, to the terminal device A100, the aggregation result given by aggregation carried out by the aggregation section 302. Thus, the terminal device A100 can obtain the result of the aggregation of the results from a plurality of terminal devices C300. That is, the terminal device A100 can collect information in the entire area where the terminal devices C300 are provided.

Further, as discussed above, the terminal device C300 in accordance with the present example embodiment may be configured as follows. That is, if the first communication section 301 receives, from the terminal device A100, an instruction to obtain information relating to a physical condition of a pedestrian, the first communication section 301 obtains the physical condition information of the user in response to reception of the instruction. Thus, the terminal device C300 in accordance with the present example embodiment makes it possible to suitably obtain the information relating to the physical condition of the pedestrian on the basis of the instruction from the terminal device A100.

(Flow of Information Transmitting Method)

Figure 9:
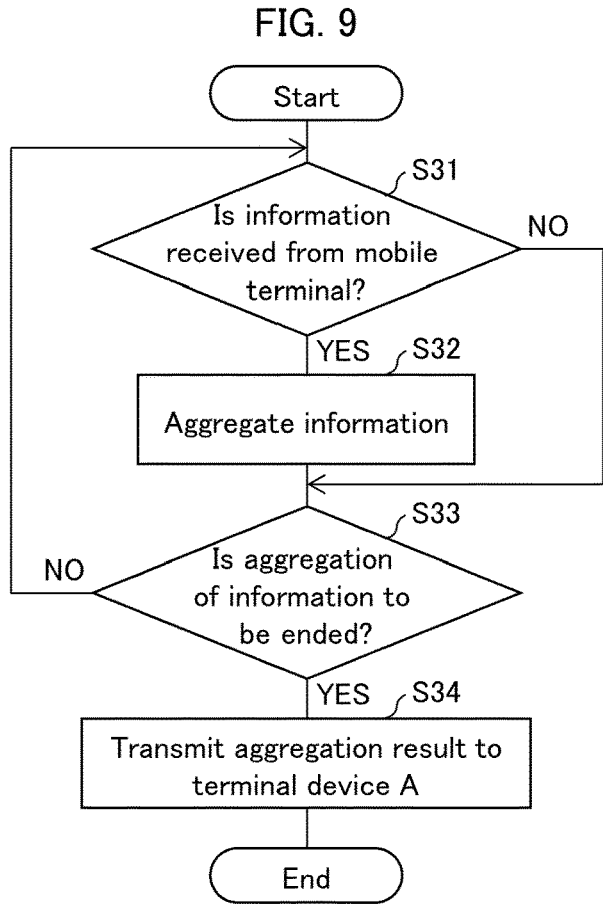
FIG. 9 is a flowchart illustrating a flow of an information processing method carried out by the mobile terminal C in accordance with the fourth example embodiment of the present invention.

FIG. 9 is a flowchart illustrating a flow of an information processing method carried out by the terminal device C300 in accordance with the fourth example embodiment of the present invention. First, the first communication section 301 determines whether or not information has been received from the mobile terminal 10 (S31). If no information has been received from the mobile terminal 10 (S31, No), the process advances to step S33.

Meanwhile, if the information has been received from the mobile terminal 10 (S31, Yes), the aggregation section 302 aggregates all the information including the information received from the mobile terminal 10 (S32), and then determines whether to end the aggregation of the information (S33).

If the aggregation of the information is not to be ended (S33, No), the process goes back to step S31 and the process of step S31 and its subsequent processes are carried out again. Meanwhile, if the aggregation of the information is to be ended (S33, Yes), the second communication section 303 transmits, to the terminal device A100, the aggregation result given by aggregation carried out by the aggregation section 302 (S34), and then the process is ended.

Note that the above-discussed information transmitting method may be configured as follows. That is, in step S31, the first communication section 301 determines whether or not the first communication section 301 has received, from the terminal device A100, an instruction to obtain information relating to a physical condition of a pedestrian; then, if the first communication section 301 determines that the instruction has been received, the first communication section 301 determines whether or not information has been received from the mobile terminal 10.

The determination on the reception of the information in step S31 and the aggregation of the information in step S32 may be carried out in parallel. Further, even while the detection in and the authentication in step S22 are continued, the aggregation of the results may be carried out periodically.

As discussed above, the information transmitting method in accordance with the present example embodiment receives, from the mobile terminal 10, (i) the body temperature information of the user and (ii) at least one of the information relating to the user and the information relating to the mobile terminal 10, aggregates the received information, and transmits the aggregation result thus obtained to the terminal device A100. Thus, the terminal device A100 can obtain the result of the aggregation of the results from a plurality of terminal devices C300. That is, the terminal device A100 can collect information in the entire area where the terminal devices C300 are provided.

The information transmitting method in accordance with the present example embodiment may execute the steps in response to reception of an instruction to obtain information relating to a physical condition of a pedestrian, the instruction being from the terminal device A100. Thus, the information transmitting method in accordance with the present example embodiment makes it possible to suitably obtain the information relating to the physical condition of the pedestrian on the basis of the instruction from the terminal device A100.

Note that the terminal device C300 can be constituted by a smaller number of constituent elements as compared to the terminal devices A100 and B200. Thus, the terminal device C300 can be designed to be smaller in size than the terminal devices A100 and B200. Thus, the terminal device C300 can be arranged suitably in various spaces.

Fifth Example Embodiment (Configuration of Network System 1)

Figure 10:
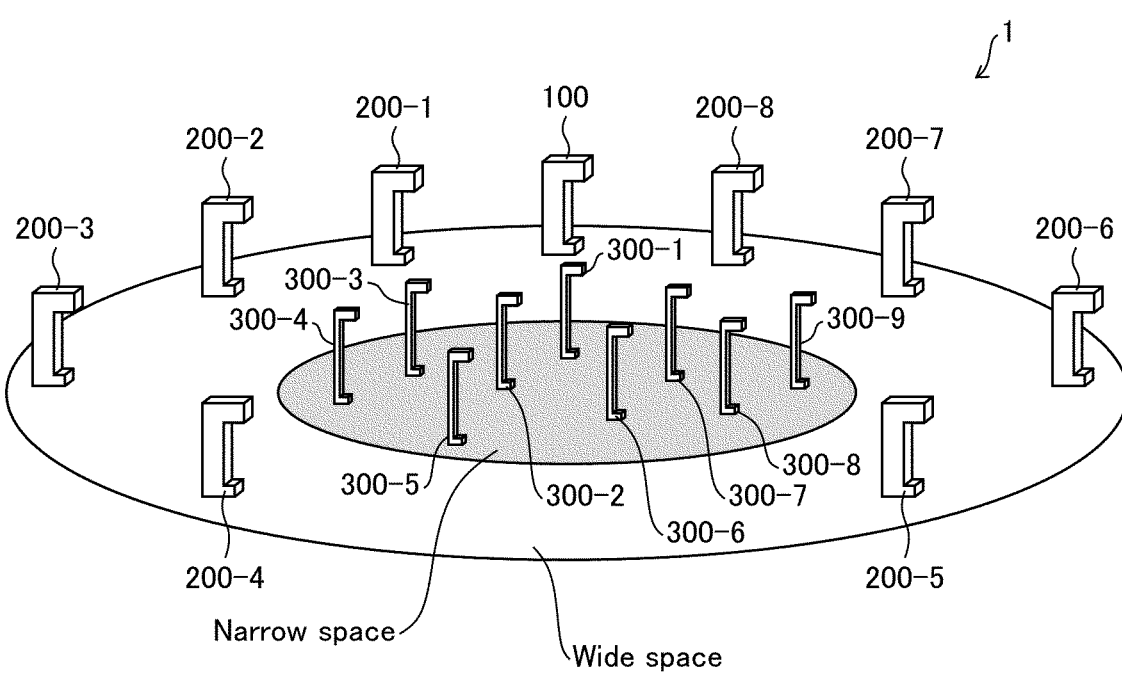
FIG. 10 is a view illustrating an example of arrangement of devices in a network system in accordance with a fifth example embodiment of the present invention.

FIG. 10 is a view illustrating an example of arrangement of devices in a network system in accordance with a fifth example embodiment of the present invention. In the example shown in FIG. 10, a target site is divided into, e.g., two spaces, a wide space and a narrow space. Then, a street-light type terminal device A100 and street-light type terminal devices B200-1 to 200-8 are set in the wide space. Meanwhile, street-light type terminal devices C300-1 to 300-9 are set in the narrow space. In order that pieces of position information of the terminal devices can be distinguished from each other, serial numbers are given to the terminal devices. The pieces of position information of the terminal devices are stored in association with the serial numbers. With this, it is possible to refer to the serial numbers so as to obtain the pieces of position information indicating positions where the terminal devices are set.

Note that the terminal devices A100, the terminal devices B200-1 to 200-8, and the terminal devices C300-1 to 300-9 are identical in configuration to the terminal device A100, the terminal devices B200, and the terminal device C300 of the above-discussed example embodiments.

In the present example embodiment, the narrow space is defined as an area having a width (e.g., approximately 600 mm to 900 mm) that allows one or two persons to pass therethrough, and the wide space is defined as an area having a width (e.g., approximately 1200 mm or more) that allows two or more persons to pass therethrough. However, this is not limitative.

Alternatively, in the present example embodiment, the narrow space may be defined as a place where many shielding objects are present or a place where communication through LTE, 4G, 5G, or the like is difficult, and the wide space may be defined as a place where the number of blocking objects is small or a place where communication through LTE, 4G, 5G, or the like can be carried out without any problem.

In the wide space, the terminal devices B200-1 to 200-8 set therein detect a person who is suspected to have an infectious disease in a detectable range. The terminal devices B200-1 to 200-8 transmit their respective aggregation results to the terminal device A100.

The terminal device A100 set in the wide space receives the aggregation results from the terminal devices B200-1 to 200-8 and the terminal devices C300-1 to 300-9. Then, the terminal device A100 refers to the aggregation results and generates a report. As will be described later, similarly to the terminal devices B200-1 to 200-8, the terminal device A100 may include a detecting section having a thermography function and an authentication section that carries out face recognition and/or the like, so as to detect, in a detectable range, a person who is suspected to have an infectious disease. Instead of the authentication section that carries out face recognition and/or the like, a biometric authentication section that carries out more general biometric authentication may be included.

Note that the arrangement of the terminal device A100, the terminal devices B200, and the terminal devices C300 in FIG. 10 is merely one example. This specific arrangement by no means limits the present example embodiment.

For example, there may be a case where, in a target site, wide spaces and narrow spaces are present in combination in a complicated manner. Further, there may be another case where, in a target site, a wide space and a narrow space cannot be clearly distinguished from each other.

In such a case, the terminal devices B200 and the terminal devices C300 may be arranged so as to be mixedly present. To be more specific, the terminal devices B200 and the terminal devices C300 may be arranged such that the areas covered by the terminal devices B200 and the areas covered by the terminal devices C300 overlap each other.

The timing of setting the terminal devices B200, the terminal device 200, and the terminal devices C300 does not limit the present example embodiment. For example, these terminal devices may be set at any timing. For another example, these terminal devices may be set at a timing when an event is held, a scheduled timing, or the like.

Figure 11:
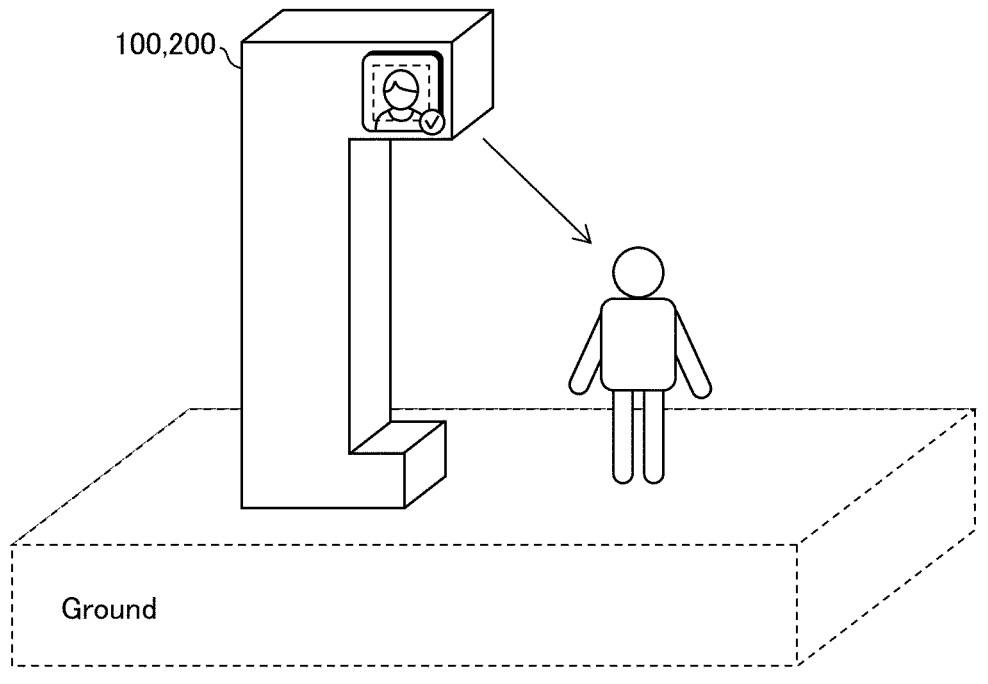
FIG. 11 is a view illustrating an example of an appearance of each of the terminal devices A and B.

FIG. 11 is a view illustrating an appearance of each of the terminal devices A100 and B200. As discussed above, in an example, each of the terminal device A100 and the terminal device B200 is arranged in the wide space and is in the shape of a street light. As shown in FIG. 11, the cameras, the detecting sections for temperature measurement, and the like are arranged at a position higher than sight lines of pedestrians. These parts are arranged taking it into account that a stress is not given to the pedestrians.

For example, in the wide space, the terminal devices C300-1 to 300-9 therein receive information from the mobile terminal 10, and the information thus received is aggregated. The terminal device C300 does not have the detecting section having a thermography function or the authentication section that carries out face recognition and/or the like. The functions of these sections are included in the terminal device 10. This, however, by no means limits the present example embodiment. Each of the terminal devices C300-1 to 300-9 may include the detecting section and the authentication section similarly to the terminal device B200.

Figure 12:
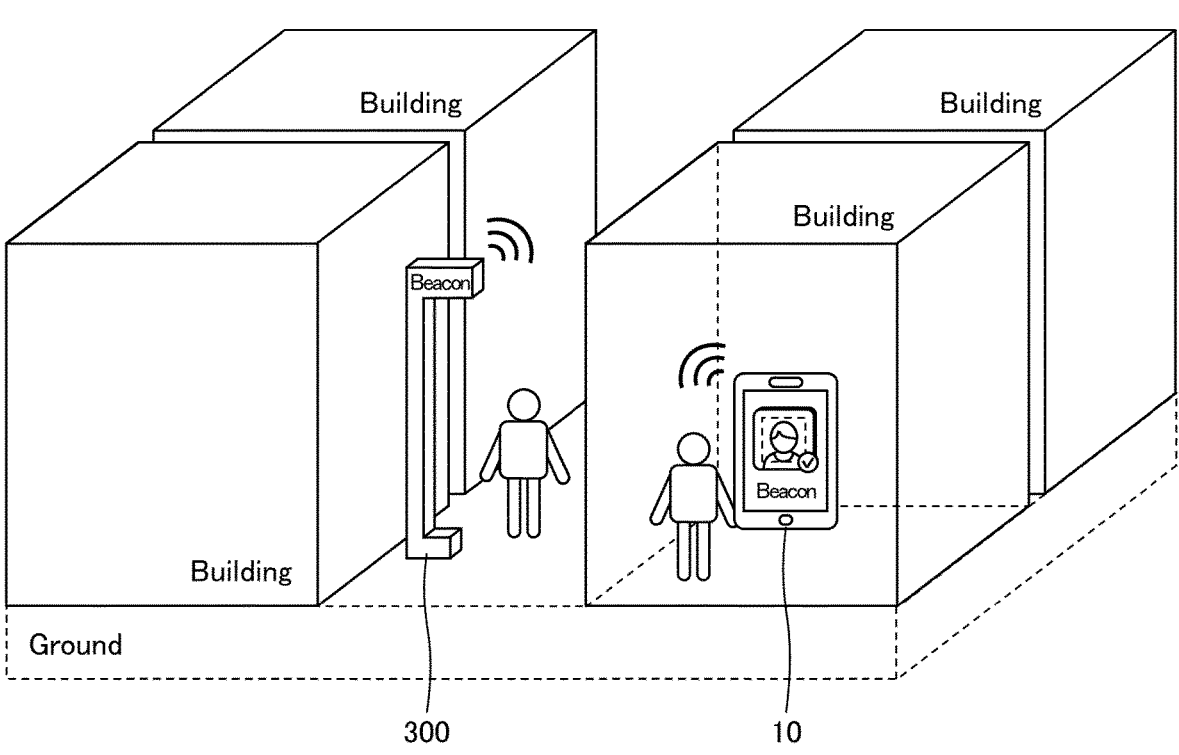
FIG. 12 is a view illustrating an example of an appearance of the terminal device C.

FIG. 12 is a view illustrating an example of an appearance of the terminal device C300. As discussed above, in an example, the terminal device C300 is arranged in the narrow space and is in the shape of a street light. The terminal device C300 communicates with the mobile terminal 10 through near field communication such as a beacon, so as to receive body temperature information of a user or an authentication result from the mobile terminal 10. As shown in FIG. 12, the narrow space has many blocking objects. Thus, the technique robust against blocking objects, such as a beacon, is used for the narrow space.

Note that the terminal device C300 is not limited to the mode in which the terminal device C300 is set in the shape of a street light. Alternatively, the terminal device C300 may have another shape or may be set in another mode. For example, the terminal device C300 may be attached to an outer wall or an inner wall of a building or may be attached to an outer side or an inner side of a traffic signal.

As discussed above, in the wide space, the terminal device A100 and the terminal device B200 are connected with each other through a high-spec local network designed for outdoors. Meanwhile, in the narrow space, the mobile terminal 10 and the terminal device C300 are connected with each other through a communication technique robust against blocking objects, such as a beacon technique. With this, it is possible to flexibly construct a communication environment in any space. Therefore, even in a case where a target site has a complicated layout, it is possible to construct a high-quality communication network in the entire site.

Further, as discussed above, the terminal device A100 obtains information relating to the difficulty in obtaining physical condition information in a place around the terminal device B200, selects one of the terminal devices B200 and C300 on the basis of the information relating to the difficulty, and obtains the information relating to the physical condition of the pedestrian from the selected terminal device.

Thus, with the network system 1 in accordance with the present example embodiment, it is possible to suitably obtain the information relating to the physical condition of the pedestrian from one of the terminal devices B200 and C300 in accordance with the difficulty in obtaining physical condition information in the place around the terminal device B200.

Figure 13:
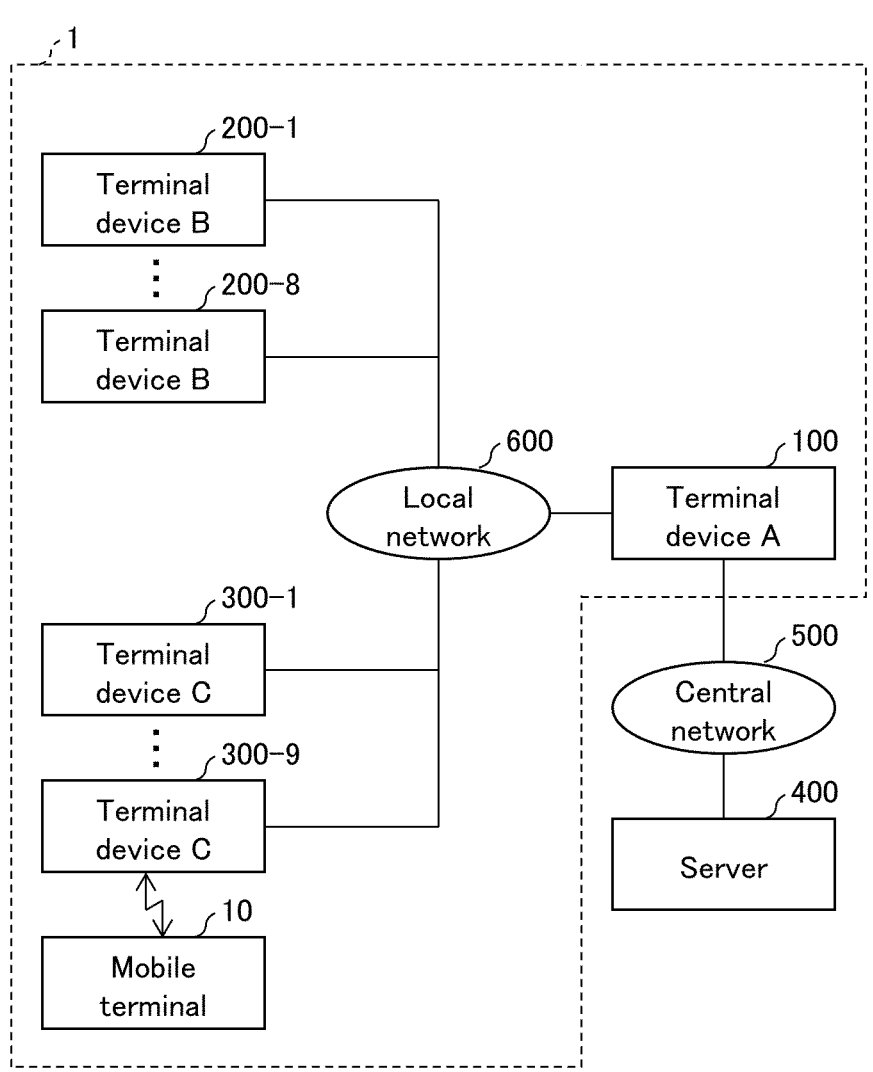
FIG. 13 is a view illustrating an example of a configuration of a network system in accordance with a fifth example embodiment of the present invention.

FIG. 13 is a view illustrating an example of a configuration of a network system 1 in accordance with a fifth example embodiment of the present invention. The network system 1 includes a terminal device A100, terminal devices B200-1 to 200-8, terminal device C300-1 to 300-9, and a mobile terminal 10.

The terminal device A100, the terminal devices B200-1 to 200-8, and the terminal devices C300-1 to 300-9 are connected with each other through a local network 600. The terminal devices C300-1 to 300-9 and the mobile terminal 10 are connected with each other through near field communication such as a beacon.

The terminal device A100 is connected, through a central network 500, a server 400 provided in an administrative agency such as a central government or a local government. The central network 500 is a wide-area communication network, such as the Internet, using a public network, Fiber To The Home (FTTH), or the like.

Figure 14:
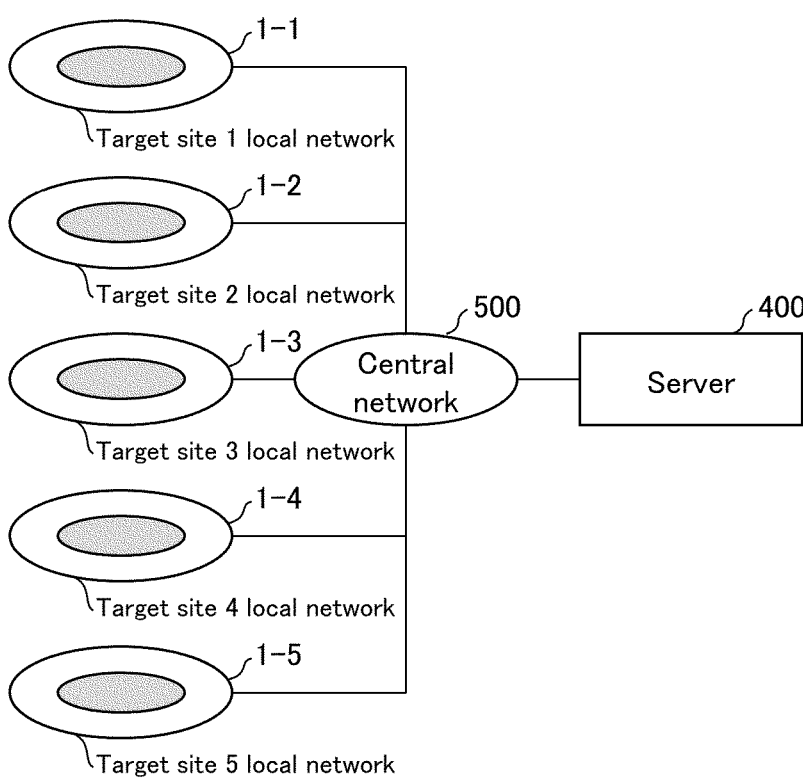
FIG. 14 is a view illustrating a case where network systems each of which is configured so as to be identical to the network system shown in FIG. 12 are arranged in a plurality of target sites.

FIG. 14 is a view illustrating a case where network systems each of which is configured so as to be identical to the network system 1 shown in FIG. 13 are arranged in a plurality of target sites. Target sites 1 to 5 are respectively provided with network systems 1-1 to 1-5. The network systems 1-1 to 1-5 are connected to the server 400, which is provided in an administrative agency such as a central government or a local government through the central network 500.

The server 400 receives reports from the terminal devices A100 respectively disposed in the network systems 1-1 to 1-5. Then, the server 400 refers to the reports and obtains information indicating, e.g., percentages of people who are suspected to have an infectious disease in the respective target sites. Then, the server 400 analyzes the information included in the reports. For example, the server 400 uses an AI function to generate, e.g., information indicating estimation of percentages of people who are suspected to have an infectious disease in the respective target sites and/or information indicating proposal of suitable support measures.

Also, the server 400 can obtain percentages of people who are suspected to have an infectious disease in the respective target sites after conduction of the suitable support measures, so as to analyze how the percentages of people who are suspected to have an infectious disease change between before and after the support measures.

As discussed above, the network system 1 in accordance with the present example embodiment is configured such that: the terminal device A100 generates a report on the basis of the aggregation results from the terminal devices B200-1 to 200-8 and the terminal devices C300-1 to 300-9, and transmits the report to the server 400. Thus, the server 400 can generate, e.g., information indicating estimation of percentages of people who are suspected to have an infectious disease in the respective target sites and/or information indicating proposal of suitable support measures.

Further, even in a situation in which an infectious disease is widely spread, the network system 1 in accordance with the present example embodiment makes it possible to simultaneously collect, in real time, pieces of information of all the plurality of areas physically distant from each other. This makes it possible to acknowledge the levels of seriousness in the respective areas and to conduct a wide, organization-level study on suitable support measures for the respective areas.

Sixth Example Embodiment (Another Example pf Configuration of Mobile Terminal)

Figure 15:
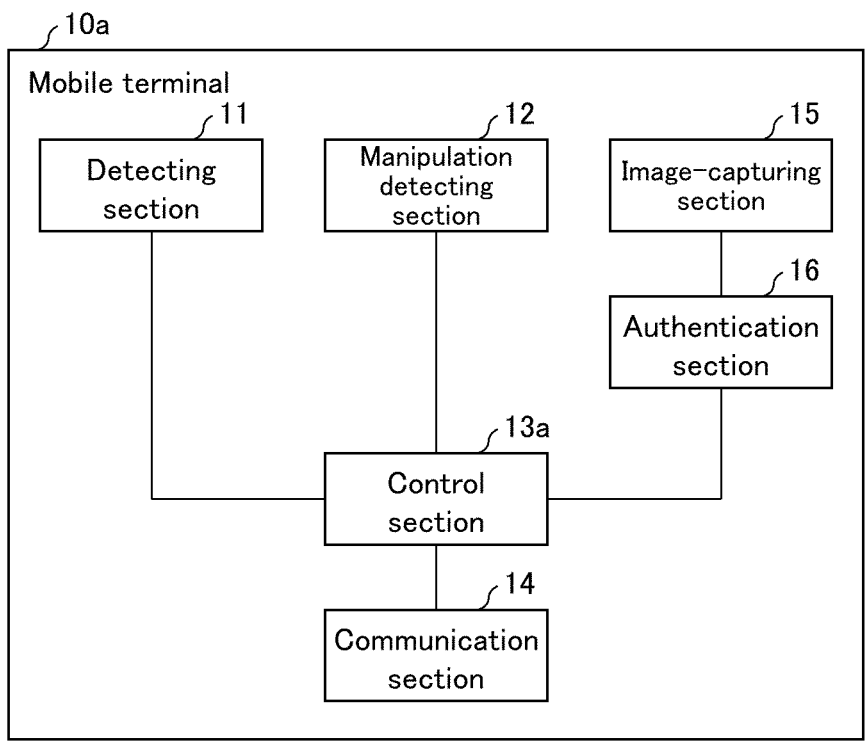
FIG. 15 is a block diagram illustrating a functional configuration of a terminal device in accordance with a sixth example embodiment of the present invention.

The following will describe, with reference to FIG. 15, a configuration of a mobile terminal 10a in accordance with the present example embodiment. FIG. 15 is a block diagram illustrating a functional configuration of the mobile terminal 10a in accordance with the sixth example embodiment of the present invention. Note that members having identical configurations and identical functions to those of the mobile terminal 10, shown in FIG. 4, in accordance with the first example embodiment are given identical reference signs, and a description thereof will be omitted.

The mobile terminal 10a includes a detecting section 11, a manipulation detecting section 12, a communication section 13a, a communication section 14, an image-capturing section 15, and an authentication section 16. The image-capturing section 15 is constituted by a camera mounted in the mobile terminal 10a, and is configured to capture an image of a user of the mobile terminal 10a.

The authentication section 16 carries out biometric authentication with use of the image of the user's face captured by the image-capturing section 15, and determines whether or not the user is an owner of the mobile terminal 10a. Further, the authentication section 16 analyzes the image of the face to recognize a coughing motion, a sneezing motion, and/or the like to detect a symptom which is suspected to be of an infectious disease. Note that the biometric authentication carried out by the authentication section 16 is not limited to face recognition. Alternatively, for example, the biometric authentication carried out by the authentication section 16 may be fingerprint recognition.

When the manipulation detecting section 12 detects manipulation on the mobile terminal 10a, the control section 13a obtains body temperature information of the user from the detecting section 11. Further, the control section 13a obtains at least one of information relating to the user and information relating to the mobile terminal 10. The information relating to the user is, for example, a symptom suspected to be of an infectious disease, the biometric authentication result, and/or the like detected by the authentication section 16. The information relating to the mobile terminal 10 is, for example, a MAC address of the mobile terminal 10a.

On the basis of the information indicating the body temperature detected by the detecting section 11 and the symptom suspected to be of an infectious disease detected by the authentication section 16, the control section 13a may comprehensively determine whether or not the user is suspected to have an infectious disease. Then, the control section 13a transmits, via the communication section 14, (i) the body temperature information of the user and (ii) at least one of the information relating to the user and the information relating to the mobile terminal 10a to the terminal device C300.

Figure 16:
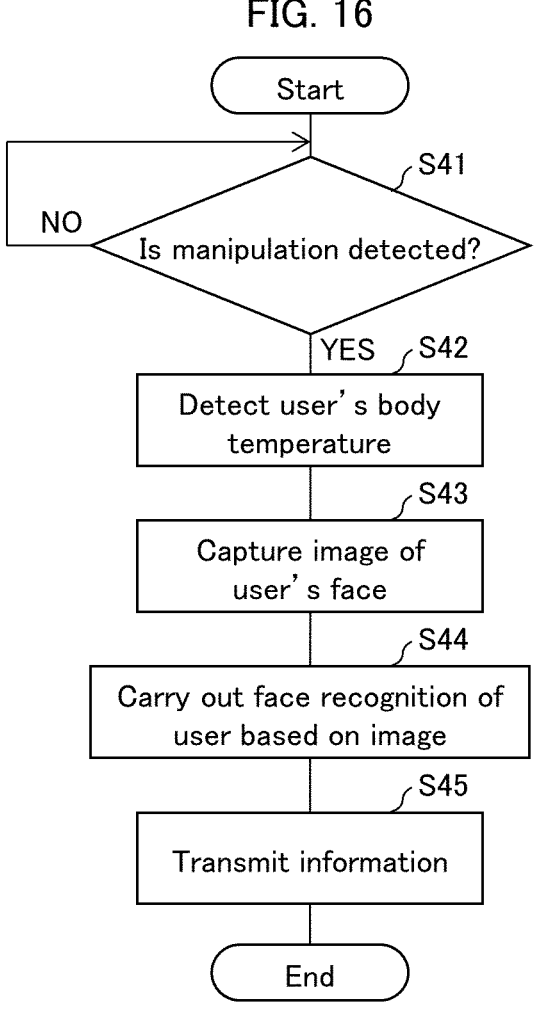
FIG. 16 is a flowchart illustrating a flow of an information transmitting method carried out by the mobile terminal in accordance with the sixth example embodiment of the present invention.

FIG. 16 is a flowchart illustrating a flow of an information transmitting method carried out by the mobile terminal 10a in accordance with the sixth example embodiment of the present invention. First, the control section 13a determines, via the manipulation detecting section 12, whether or not the mobile terminal 10a is manipulated (S41). If it is determined that the mobile terminal 10a is not manipulated (S41, No), the process in step S41 is carried out again.

Meanwhile, if it is determined that the mobile terminal 10a is manipulated (S41, Yes), the control section 13a detects, via the detecting section 11, a body temperature of the user (S42). Then, the image-capturing section 15 captures an image of the user's face (S43).

Next, the authentication section 16 carries out face recognition of the user with use of the image of the user's face captured by the image-capturing section 15 (S44). The control section 13a obtains at least one of information relating to the user and information relating to the mobile terminal 10a. Then, the control section 13a transmits, via the communication section 14, (i) the body temperature information of the user and (ii) at least one of the information relating to the user and the information relating to the mobile terminal 10a to the terminal device C300 (S45).

As discussed above, the mobile terminal 10a in accordance with the present example embodiment is configured such that the authentication section 16 analyzes an image of a face to detect a symptom suspected to be of an infectious disease. This enables the mobile terminal 10a to transmit, to the terminal device C300, information given as a result of comprehensive consideration of the user's body temperature information and the symptom suspected to be of an infectious disease.

Seventh Example Embodiment (Example of Specific Configuration of Terminal Device A)

Figure 17:
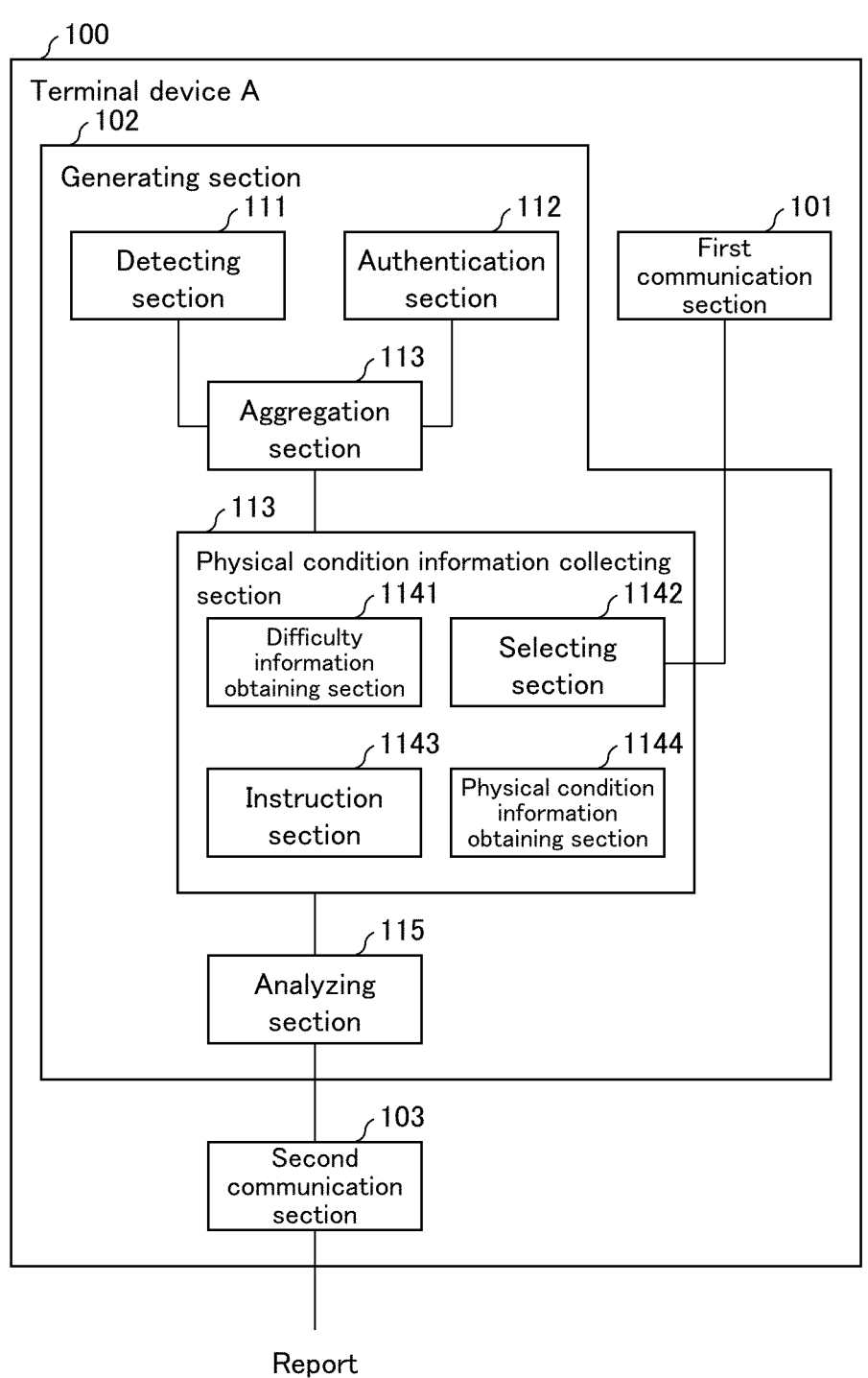
FIG. 17 is a block diagram illustrating a functional configuration of a terminal device A in accordance with a seventh example embodiment of the present invention.

The following will describe, with reference to FIG. 17, a specific configuration of a terminal device A100 in accordance with the present example embodiment. FIG. 17 is a block diagram illustrating a functional configuration of the terminal device A100 in accordance with a seventh example embodiment of the present invention.

As shown in FIG. 17, the terminal device A100 in accordance with the present example embodiment includes a first communication section 101, a generating section 102, and a second communication section 103.

The first communication section 101 communicates with the above-discussed terminal devices B200 and C300 through a local network such as Local Area Network (LAN). In an example, the first communication section 101 receives, from the terminal device C300, a result of aggregation of (i) body temperature information of a user and (ii) at least one of information relating to the user and information relating to a mobile terminal 10. In an example, the first communication section 101 receives, from the terminal device B200, information given by aggregation of body temperature information of a pedestrian and information given by aggregation of symptoms suspected to be of an infectious disease. Note that the first communication section 101 may carry out communication through a wired or wireless network.

The generating section 102 generates a report regarding people who are suspected to have an infectious disease in a given area on the basis of the aggregation results received from the terminal devices B200 and C300. This report includes at least a percentage of the people who are suspected to have an infectious disease in the given area.

The report may be written in a natural language so that a human can read the report easily. Alternatively, the report may be written in a computer language so that mainly a computer can read the report easily. The generating section 102 may be configured to generate the above report with use of AI (to be more specific, a learned generation model) having an automatic text generating function. A detailed configuration of the generating section 102 will be described later.

The second communication section 103 communicates, through a wide-area communication network (central network) such as the Internet, with a server set in a site of an administrative agency such as a central government or a local government. The second communication section 103 transmits, to the server, the report generated by the generating section 102. Note that the second communication section 103 may carry out communication through a wired or wireless network.

(Generating Section)

As shown in FIG. 17, the generating section 102 includes a detecting section 111, an authentication section 112, an aggregation section 113, a physical condition information collecting section 114, and an analyzing section 115. The detecting section 111 has a thermography function, and detects a body temperature of a pedestrian who is a subject to be monitored in a detectable range.

The authentication section 112 obtains an image of the pedestrian's face captured by a camera or the like. Then, the authentication section 112 analyzes the image of the face to recognize a coughing motion, a sneezing motion, and/or the like to detect a symptom which is suspected to be of an infectious disease.

On the basis of the information indicating the body temperature detected by the detecting section 111 and the symptom suspected to be of an infectious disease detected by the authentication section 112, the aggregation section 113 comprehensively determines whether or not a pedestrian is suspected to have an infectious disease, and generates information given by aggregation of the determination results.

As shown in FIG. 17, the physical condition information collecting section 114 includes a difficulty information obtaining section 1141, a selecting section 1142, an instruction section 1143, and a physical condition information obtaining section 1144.

(Difficulty Information Obtaining Section)

The difficulty information obtaining section 1141 obtains information relating to the difficulty in obtaining physical condition information in a place around the terminal device B200.

Here, the "information relating to the difficulty in obtaining the physical condition information in the place around the terminal device B200" refers to information indicating the degree of ease of the terminal device B200 obtaining the physical condition information. In an example, the information relating to the difficulty can be obtained from the result of detection carried out at least one of the detecting section 201 and other means included in the terminal device B200. For example, the information relating to the difficulty can be expressed by a difference between:

a total number of living bodies recognized, through biometric authentication, by the detecting section 201 included in the terminal device B200 in a predetermined period; and a total number of faces recognized by the detecting section 201 in the predetermined period.

Here, a specific example of the predetermined period may be approximately one minute to approximately an hour. This, however, by no means limits the present example embodiment. In other words, the information relating to the difficulty in obtaining the physical condition information in the place around the terminal device B is information that can be updated in real time in a cycles of the predetermined period.

Thus, in an example, the difficulty information obtaining section 1141 can obtain information that indicates, in real time, the difficulty in obtaining the physical condition information in the place around the terminal device B200.

As the information relating to the difficulty, information relating to a status of communication between a mobile terminal of a user and the terminal device C300 may be used. In the present example embodiment, there is no limitation on specific arrangement of the terminal devices B200 and C300. For example, in a case where the terminal devices B200 and C300 are arranged mixedly, information relating to a status of communication between the mobile terminal 10, 10a of the user and the terminal device C may be suitably used as the information relating to the difficulty.

The information relating to the status of the communication is also information that can be updated in real time. Thus, also with this configuration, the difficulty information obtaining section 1141 can obtain information that indicates, in real time, the difficulty in obtaining the physical condition information in the place around the terminal device B200.

(Selecting Section)

The selecting section 1142 selects one of the terminal devices B200 and C300 on the basis of the information relating to the difficulty in obtaining the physical condition information obtained by the difficulty information obtaining section 1141. Here, a specific example of the selecting process carried out by the selecting section 1142 may be as follows. That is, in a case where the information relating to the difficulty in obtaining the physical condition information indicates that the degree of difficulty in obtaining the physical condition information is higher than a given degree, the selecting section 1142 selects the terminal device C300. This, however, by no means limits the present example embodiment. Further, in one example, in a case where the information relating to the difficulty in obtaining the physical condition information indicates that the degree of difficulty in obtaining the physical condition information is not higher than the given degree, the selecting section 1142 may select the terminal device B200.

To be more specific, the selecting section 1142 may be configured to determine (i) that the degree of difficulty in obtaining the physical condition information is higher than a given degree in a case where a difference obtained by subtracting a total number of faces recognized by the detecting section 201 in the predetermined period from a total number of living bodies recognized, through biometric authentication, by the detecting section 201 included in the terminal device B200 in a predetermined period is not less than a given value and (ii) that the degree of difficulty in obtaining the physical condition information is not higher than the given degree in a case where the above difference is less than the given value.

Alternatively, the selecting section 1142 may be configured to determine (i) that the degree of difficulty in obtaining the physical condition information is higher than a given degree in a case where information relating to a status of communication between a mobile terminal of a user and the terminal device C300 indicates that the communication status is poorer than a given degree and (ii) that the degree of difficulty in obtaining the physical condition information is not higher than the given degree in a case where the above information indicates that the communication status is better than the given value.

(Instruction Section)

Via the first communication section 101, the instruction section 1143 gives, to one of the terminal devices B200 and C300 selected by the selecting section 1142, an instruction to obtain information relating to a physical condition of a pedestrian.

(Target Information Obtaining Section 1144)

The physical condition information obtaining section 1144 obtains, via the first communication section 101, the information relating to the physical condition of the pedestrian from one of the terminal devices B200 and C300 which has been selected by the selecting section 1142 and which has received the instruction from the instruction section 1143.

In the above-described manner, the physical condition information collecting section 114 collects contents including the aggregation results relating to the physical condition information supplied from the terminal devices B200 and C300 and received by the first communication section 101, and collects the aggregation result generated by the aggregation section 113.

The analyzing section 115 analyzes the aggregation result collected by the content collecting section 114, and generates a report on people who are suspected to have an infectious disease in a given area. This report includes at least a percentage of the people who are suspected to have an infectious disease in the given area.

As discussed above, the terminal device A100 in accordance with the present example embodiment includes:

the first communication section 101 that communicates with the terminal device B200 (first terminal device) including the detecting means that detects information relating to a physical condition of a pedestrian and with the terminal device C300 (second terminal device) including the obtaining means that obtains information relating to a physical condition of the pedestrian from a mobile terminal of the pedestrian;

the difficulty information obtaining section 1141 that obtains information relating to the difficulty in obtaining physical condition information in a place around the terminal device B200;

the selecting section 1142 that selects one of the terminal devices B200 and C300 on the basis of the information relating to the difficulty in obtaining the physical condition information; and the physical condition information obtaining section 1144 that obtains, from the terminal device selected by the selecting section 1142, the information relating to the physical condition of the pedestrian.

The terminal device A100 configured as above refers to the information relating to the difficulty in obtaining the physical condition information in the place around the terminal device B200, and selects one of the terminal devices B200 and C300; then, the terminal device A100 obtains the information relating to the physical condition of the pedestrian from the selected terminal device. Therefore, it is possible to suitably collect the information relating to the physical condition of the pedestrian in accordance with the difficulty in obtaining the physical condition information.

As discussed above, the terminal device A100 in accordance with the present example embodiment is configured such that the generating section 102 generates a report including at least a percentage of people who are suspected to have an infectious disease in a given area on the basis of the aggregation result received by the first communication section 101. Thus, in a server set in a site of an administrative agency such as a central government or a local government, it is possible to acknowledge percentages of people who are suspected to have an infectious disease in respective areas by referring to a received report, thereby making it possible to generate a proposal of a suitable support measure and/or the like.

(Flow of Information Transmitting Method)

Figure 18:
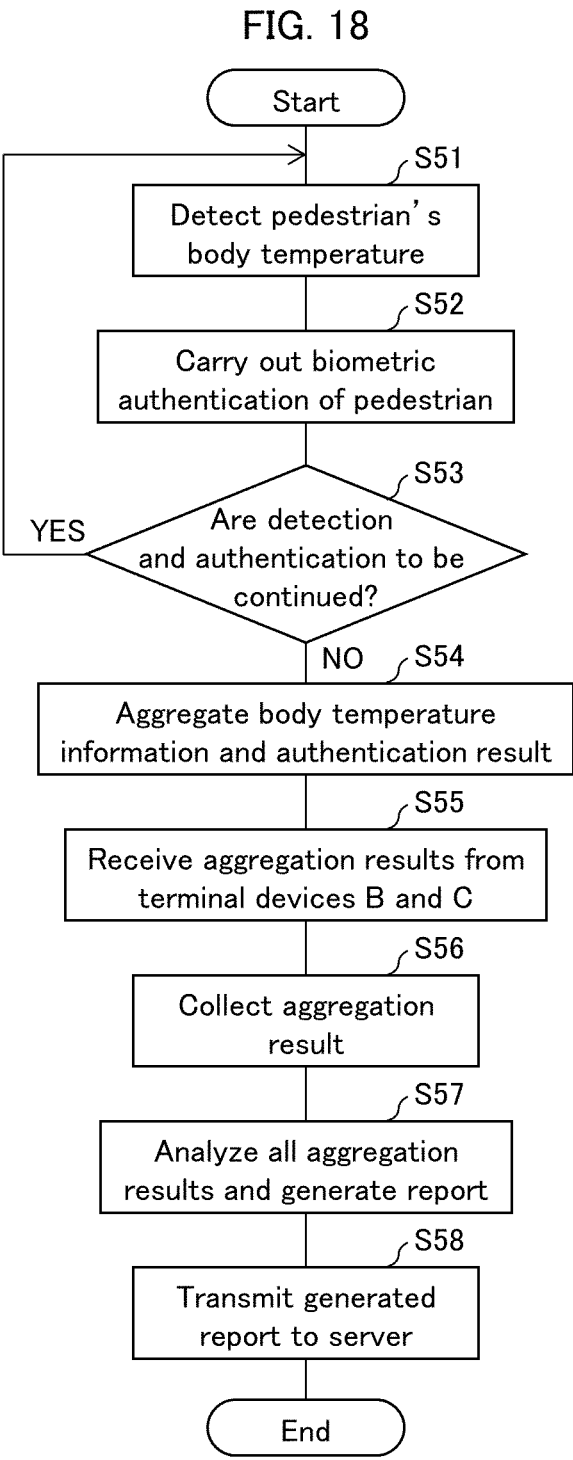
FIG. 18 is a flowchart illustrating a flow of an information processing method carried out by the mobile terminal A in accordance with the seventh example embodiment of the present invention.

FIG. 18 is a flowchart illustrating a flow of an information processing method carried out by the terminal device A100 in accordance with the seventh example embodiment of the present invention. First, the detecting section 111 detects a body temperature of a pedestrian (S51). Then, the authentication section 112 carries out biometric authentication of the pedestrian (S52).

Next, the aggregation section 113 determines whether to continue the body temperature detection by the detecting section 111 and the biometric authentication by the authentication section 112 (S53). If the detection and authentication are to be continued (S53, Yes), the process returns to step S51 and the process of step S51 and its subsequent processes are carried out again.

If the detection and authentication are not to be continued (S53, No), the aggregation section 113 aggregates the body temperature information and the authentication result (S54). Then, the content collecting section 114 collects contents including the aggregation results relating to the physical condition information from the terminal devices B200 and C300 received by the first communication section 101 (S55), and collects the aggregation result generated by the aggregation section 113 (S56).

Next, the analyzing section 115 analyzes the aggregation result collected by the content collecting section 114, and generates a report. Then, the second communication section 103 transmits, to the server 400, the report generated by the analyzing section 115 (S58).

(Details of Physical Condition Information Obtaining Process)

Figure 19:
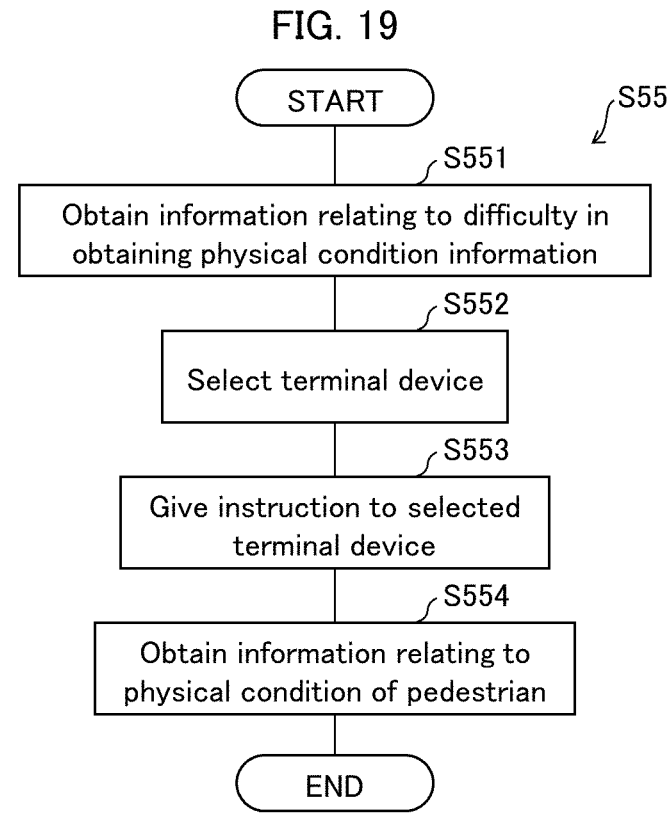
FIG. 19 is a flowchart illustrating a flow of a target information obtaining method carried out by the mobile terminal A in accordance with the seventh example embodiment of the present invention.

The following description will discuss, with reference to FIG. 19, details of the physical condition information obtaining process carried out in the above-discussed step S55. FIG. 19 is a flowchart illustrating details of the physical condition information obtaining process in step S55.

(Step S551)

First, in step S551, the difficulty information obtaining section 1141 of the terminal device A100 obtains information relating to the difficulty in obtaining physical condition information in a place around the terminal device B200 including the detecting section 201 that detects information relating to a physical condition of a pedestrian. The "information relating to the difficulty in obtaining the physical condition information" has been discussed above, and therefore a description thereof will be omitted here.

(Step S552)

Subsequently, in step S552, the selecting section 1142 of the terminal device A100 selects one of the terminal devices B200 and C300 on the basis of the information relating to the difficulty in obtaining the physical condition information obtained in step S551. The selecting process carried out by the selecting section 1142 is identical to the selecting process discussed above.

(Step S553)

Subsequently, in step S553, via the first communication section 101, the instruction section 1143 of the terminal device A100 gives, to one of the terminal devices B200 and C300 selected by the selecting section 1142, an instruction to obtain information relating to a physical condition of a pedestrian.

(Step S554)

Then, in step S554, the physical condition information obtaining section 106 of the terminal device A100 obtains the information relating to the physical condition of the pedestrian from the terminal device which has been selected in step S552 and which has received the instruction in step S553.

With the information processing method configured as above, it is possible to attain similar effects to those given by the terminal device A100 in accordance with the present example embodiment.

Software Implementation Example

Control blocks (particularly, the control section 13, 13*a*, the authentication section 16, 112, 202, the generating section 102, 203, the authentication section 113, 302, the content collecting section 114, and the analyzing section 115) of the mobile terminal 10, the terminal device A100, the terminal device B200, and the terminal device C300 can be realized by a logic circuit (hardware) provided in an integrated circuit (IC chip) or the like or can be alternatively realized by software.

Figure 20:
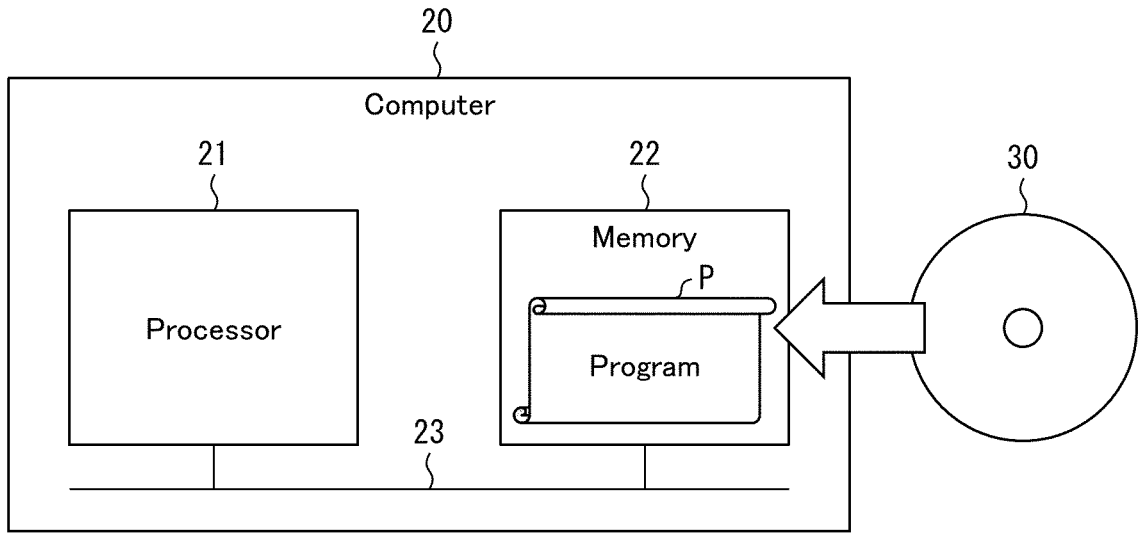
FIG. 20 is a view illustrating an example of a hardware configuration of a computer.

In the latter case, each of the mobile terminal 10, the terminal device A100, the terminal device B200, and the terminal device C300 includes a computer that executes instructions of a program that is software realizing the foregoing functions. The computer, for example, includes at least one processor (control device) and at least one computer-readable storage medium storing the program. FIG. 20 is a view illustrating an example of a hardware configuration of the computer. A computer 20 includes a processor 21 and a memory 22 storing a program P stored in a storage medium 30, the processor 21 and the memory 22 being connected with each other via an internal bus 23.

An example object of the present invention can be achieved by the processor 21 of the computer 20 reading and executing the program P stored in the storage medium 30. Examples of the processor 21 encompass a central processing unit (CPU). Examples of the storage medium 30 encompass a "non-transitory tangible medium" such as a compact disc-read only memory (CD-ROM), a digital versatile disc (DVD), a read only memory (ROM), a tape, a disk, a card, a semiconductor memory, and a programmable logic circuit. The computer may further include a random access memory (RAM) or the like as the memory 22 in which the program P is loaded. Further, the program P may be made available to the computer 20 via any transmission medium (such as a communication network and a broadcast wave) which allows the program P to be transmitted. Note that an aspect of the present invention can also be achieved in the form of a computer data signal in which the program P is embodied via electronic transmission and which is embedded in a carrier wave.

Fields to which the Present Invention is Applicable

It is considered that the present invention can be used in saving a human's life after occurrence of a natural disaster such as an earthquake or tsunami. The present invention is considered to be applicable to a method for finding a person (disaster victim) who retains consciousness but is confined in a building collapsed by a disaster and cannot escape therefrom.

Further, the terminal devices A100 and C300 of the present invention can be temporarily set after occurrence of a natural disaster. As a disaster control measure, before occurrence of a disaster, the mobile terminal 10 can be provided with a biometric authentication (fingerprint recognition) function and a beacon application as biometric authentication instead of face recognition and body temperature detection. Then, when the person falls victim to a disaster and is subjected to fingerprint recognition via the beacon application having the fingerprint recognition technique, identification information and position information of the mobile terminal 10 are transmitted to a beacon of the terminal device C300, which is temporarily set.

The terminal device C300 transmits all the pieces of information to the terminal device A100. Consequently, a rescuer can acknowledge where the disaster victim is and from which mobile terminal 10 the disaster victim transmits a reaction (SOS). Thus, the rescuer can go to the disaster victim preferentially and quickly.

Supplementary Note 1

The present invention is not limited to the example embodiments, but can be altered by a skilled person in the art within the scope of the claims. The present invention also encompasses, in its technical scope, any embodiment derived by combining technical means disclosed in differing embodiments.

Supplementary Note 2

Some or all of the above embodiments can be described as below. Note, however, that the present invention is not limited to aspects described below.

A mobile terminal in accordance with a first aspect includes: a detecting means that detects a body temperature of a user; a communication means that communicates with a terminal device; and a control means that transmits, to the terminal device via the communication means, (i) information indicating the body temperature of the user detected by the detecting means and (ii) at least one of information relating to the user and information relating to the mobile terminal, the transmission being carried out in response to manipulation on the mobile terminal.

According to the above configuration, with the terminal device, it is possible to easily collect information relating to a person who is suspected to have an infectious disease.

A mobile terminal in accordance with a second aspect, which includes the configuration of the first aspect, is configured such that: the manipulation is pressing of a hardware button of the mobile terminal.

According to the above configuration, the information such as the body temperature information is transmitted to the terminal device in response to pressing of a hardware button which is to be used for, e.g., unlocking. This can reduce the frequency of transmission of the information to the terminal device.

A mobile terminal in accordance with a third aspect, which includes the configuration of the first or second aspect, is configured such that: the information transmitted from the control means to the terminal device includes the information relating to the user, the mobile terminal further includes an authentication means that carries out biometric authentication of the user, and the information relating to the user is a result of biometric authentication carried out by the authentication means.

According to the above configuration, the information relating to the user is the result of the biometric authentication. Thus, with the terminal device, it is possible to specify the user of the mobile terminal.

A mobile terminal in accordance with a fourth aspect, which includes the configuration of the third aspect, further includes: an image-capturing means that captures an image, wherein the authentication means detects, on the basis of the image of the user's face captured by the image-capturing means, a symptom which is suspected to be of an infectious disease, and the control means transmits, to the terminal device via the communication means, the information indicating the body temperature of the user detected by the detecting means and the symptom suspected to be of an infectious disease detected by the authentication means.

According to the above configuration, the body temperature information of the user and the symptom suspected to be of an infectious disease are transmitted to the terminal device via the communication means. Thus, with the terminal device, it is possible to determine whether or not the user of the mobile terminal is suspected to have an infectious disease.

A mobile terminal in accordance with a fifth aspect, which includes the configuration of any one of the first to fourth aspects, is configured such that: the information relating to the mobile terminal is identification information of the mobile terminal.

According to the above configuration, it is possible to specify the user of the mobile terminal.

A terminal device in accordance with a sixth aspect is a terminal device that carries out near field communication with a mobile terminal, the terminal device including: a first communication means that receives, from the mobile terminal through near field communication, (i) information indicating a body temperature of a user and (ii) at least one of information relating to the user and information relating to the mobile terminal; an aggregation means that aggregates the information received via the first communication means; and a second communication means that transmits, to another terminal device, a result of the aggregation carried out by the aggregation means.

According to the above configuration, the aggregation means aggregates the information received from the mobile terminal, and the second communication means transmits the aggregation result to another terminal device. Thus, the another terminal device can collect information in the entire area where the terminal device is provided.

A terminal device in accordance with a seventh aspect, which includes the configuration of the sixth aspect, is configured such that: the information received by first communication means includes the information relating to the user, and the information relating to the user includes a result of biometric authentication carried out on the user.

According to the above configuration, the information relating to the user is the result of the biometric authentication. Thus, with the terminal device, it is possible to specify the user of the mobile terminal.

A terminal device in accordance with an eighth aspect, which includes the configuration of the seventh aspect, is configured such that: the information relating to the user includes information relating a symptom suspected to be of an infectious disease detected on the basis of an image of a face of the user.

According to the above configuration, with the terminal device, it is possible to determine whether or not the user of the mobile terminal is suspected to have an infectious disease.

A terminal device in accordance with a ninth aspect, which includes the configuration of any one of the sixth to eighth aspects, is configured such that: the information relating to the mobile terminal is identification information of the mobile terminal.

According to the above configuration, it is possible to specify the user of the mobile terminal.

A terminal device in accordance with a tenth aspect is a terminal device that communicates with another mobile terminal, the terminal device including: a first communication means that receives, from the another terminal device, a result of aggregation of (i) information indicating a body temperature of a user and (ii) at least one of information relating to the user and information relating to the mobile terminal; a generating means that generates, on the basis of the result of the aggregation received by the first communication means, a report including at least a percentage of people who are suspected to have an infectious disease in a given area; and a second communication means that transmits, to a server, the report generated by the generating means.

According to the above configuration, in the server, it is possible to acknowledge, by referring to the report thus received, percentages of people who are suspected to have an infectious disease in respective areas.

A terminal device in accordance with an eleventh aspect, which includes the configuration of the tenth aspect, is configured such that: the result of the aggregation received by the first communication means includes the information relating to the user, and the information relating to the user includes a result of biometric authentication carried out on the user.

According to the above configuration, the information relating to the user is the result of the biometric authentication. Thus, with the terminal device, it is possible to specify the user of the mobile terminal.

A terminal device in accordance with a twelfth aspect, which includes the configuration of the eleventh aspect, is configured such that: the information relating to the user includes information relating to a symptom suspected to be of an infectious disease detected om the basis of an image of a face of the user.

According to the above configuration, with the terminal device, it is possible to determine whether or not the user of the mobile terminal is suspected to have an infectious disease.

A terminal device in accordance with a thirteenth aspect, which includes the configuration of any one of the tenth to twelfth aspects, is configured such that: the information relating to the mobile terminal is identification information of the mobile terminal.

According to the above configuration, it is possible to specify the user of the mobile terminal.

A terminal device in accordance with a fourteenth aspect includes: a detecting means that detects a body temperature of a pedestrian; an authentication means that detects, on the basis of an image of a face of the pedestrian, a symptom suspected to be of an infectious disease; a generating means that generates information given by aggregation of (i) information indicating the body temperature of the pedestrian detected by the detecting means and (ii) the symptom suspected to be of an infectious disease detected by the authentication means; and a communication means that transmits, to the another terminal device, the information generated by the generating means.

According to the above configuration, another terminal device can collect information in the entire area where the another terminal device is provided.

A network system in accordance with a fifteenth aspect is a network system that includes a mobile terminal and a terminal device carrying out near field communication with the mobile terminal, the mobile terminal including: a detecting means that detects a body temperature of a user; a first communication means that carries out near field communication with the terminal device; a control means that transmits, to the terminal device via the first communication means, (i) information indicating the body temperature of the user detected by the detecting means and (ii) at least one of information relating to the user and information relating to the mobile terminal, the transmission being carried out in response to manipulation on the mobile terminal, and the terminal device including: a second communication means that receives, from the mobile terminal through near field communication, (i) the information indicating the body temperature of the user and (ii) at least one of the information relating to the user and the information relating to the mobile terminal; an aggregation means that aggregates the information received via the second communication means; and a third communication means that transmits, to another terminal device, a result of the aggregation carried out by the aggregation means.

According to the above configuration, with the terminal device, it is possible to easily collect information relating to a person who is suspected to have an infectious disease. Further, the another terminal device ca collect information in the entire area where the terminal device is provided.

A network system in accordance with a sixteenth aspect is a network system that includes a first terminal device and a second terminal device communicating with the first terminal device, the first terminal device including: a first communication means that receives, from a mobile terminal through near field communication, (i) information indicating a body temperature of a user and (ii) at least one of information relating to the user and information relating to the mobile terminal; an aggregation means that aggregates the information received via the first communication means; and a second communication means that transmits, to the second terminal device, a result of the aggregation carried out by the aggregation means, and the second terminal device including: a third communication means that receives the result of the aggregation from the first terminal device; a generating means that generates, on the basis of the result of the aggregation received by the third communication means, a report including at least a percentage of people who are suspected to have an infectious disease in a given area; and a fourth communication means that transmits, to a server, the report generated by the generating means.

According to the above configuration, with the second terminal device, it is possible to collect information in the entire area where the first terminal device is provided. Further, the server can acknowledge percentages of people who are suspected to have an infectious disease in respective areas.

An information transmitting method in accordance with a seventeenth aspect includes the steps of: detecting a body temperature of a user in response to manipulation on a mobile terminal; and transmitting, to a terminal device, (i) information indicating the body temperature of the user thus detected and (ii) at least one of information relating to the user and information relating to the mobile terminal.

According to the above configuration, with the terminal device, it is possible to easily collect information relating to a person who is suspected to have an infectious disease.

A computer program in accordance with an eighteenth aspect is a computer program causing a computer to execute an information transmitting method that includes the steps of: detecting a body temperature of a user in response to manipulation on a mobile terminal; and transmitting, to a terminal device, (i) information indicating the body temperature of the user thus detected and (ii) at least one of information relating to the user and information relating to the mobile terminal.

According to the above configuration, with the terminal device, it is possible to easily collect information relating to a person who is suspected to have an infectious disease.

An information transmitting method in accordance with a nineteenth aspect includes the steps of: receiving, from a mobile terminal through near field communication, (i) information indicating a body temperature of a user and (ii) at least one of information relating to the user and information relating to the mobile terminal; aggregating the information thus received; and transmitting, to another terminal device, a result of the aggregation.

According to the above configuration, another terminal device can collect information in the entire area where the terminal device is provided.

A computer program in accordance with a twentieth aspect is a computer program causing a computer to execute an information transmitting method that includes the steps of: receiving, from a mobile terminal through near field communication, (i) information indicating a body temperature of a user and (ii) at least one of information relating to the user and information relating to the mobile terminal; aggregating the information thus received; and transmitting, to another terminal device, a result of the aggregation.

According to the above configuration, another terminal device can collect information in the entire area where the terminal device is provided.

An information transmitting method in accordance with a twenty-first aspect includes the steps of: receiving, from a terminal device, a result of aggregation of (i) information indicating a body temperature of a user and (ii) at least one of information relating to the user and information relating to a mobile terminal; generating, on the basis of the result of the aggregation thus received, a report including at least a percentage of people who are suspected to have an infectious disease in a given area; and transmitting the generated report to a server.

According to the above configuration, in the server, it is possible to acknowledge, by referring to the report thus received, percentages of people who are suspected to have an infectious disease in respective areas.

A computer program in accordance with a twenty-second aspect is a computer program causing a computer to execute an information transmitting method that includes the steps of: receiving, from a terminal device, a result of aggregation of (i) information indicating a body temperature of a user and (ii) at least one of information relating to the user and information relating to the mobile terminal; generating, on the basis of the result of the aggregation thus received, a report including at least a percentage of people who are suspected to have an infectious disease in a given area; and transmitting, to a server, the report thus generated.

According to the above configuration, in the server, it is possible to acknowledge, by referring to the report thus received, percentages of people who are suspected to have an infectious disease in respective areas.

An information transmitting method in accordance with a twenty-third aspect includes the steps of: detecting a body temperature of a pedestrian; detecting, on the basis of an imager of a face of the pedestrian, a symptom suspected to be of an infectious disease; generating information given by aggregation of (i) information indicating the body temperature of the pedestrian thus detected and (ii) the symptom suspected to be of the infectious disease; and transmitting, to a terminal device, the information thus generated.

According to the above configuration, the terminal device can collect information in the entire area where the terminal device is provided.

A computer program in accordance with a twenty-fourth aspect is a computer program causing a computer to execute an information transmitting method that includes the steps of: detecting a body temperature of a pedestrian; detecting, on the basis of an image of a face of the pedestrian, a symptom suspected to be of an infectious disease; generating information given by aggregation of (i) information indicating the body temperature of the pedestrian having been detected and (ii) the symptom suspected to be of the infectious disease having been detected; and transmitting, to a terminal device, the information thus generated.

According to the above configuration, the terminal device can collect information in the entire area where the terminal device is provided.

Supplementary Note 3

Further, some or all of the above embodiments can be expressed as below.

A mobile terminal including at least one processor, the at least one processor executing: a detecting process of detecting a body temperature of a user; a communication process of communicating with a terminal device; and a control process of carrying out, in response to manipulation on the mobile terminal, the communication process to transmit (i) information indicating the body temperature of the user detected by the detecting process and (ii) at least one of information relating to the user and information relating to the mobile terminal to a terminal device.

Note that the mobile terminal may further include a memory. In the memory, a program causing the processor to execute the detecting process, the communication process, and the control process may be stored. The program may be stored in a non-transitory, tangible storage medium capable of being read by a computer.

A terminal device including at least one processor, the at least one processor executing: a receiving means that receives, from a mobile terminal through near field communication, (i) information indicating a body temperature of a user and (ii) at least one of information relating to a user and information relating to the mobile terminal; an aggregation process of aggregating the information by the receiving process; and a transmitting process of transmitting, to another terminal device, a result of the aggregation carried out by the aggregation process.

Note that the terminal device may further include a memory. In the memory, a program causing the processor to execute the receiving process, the aggregation process, and the transmitting process may be stored. The program may be stored in a non-transitory, tangible storage medium capable of being read by a computer.

A terminal device including at least one processor, the at least one processor being a terminal device communicate with another terminal device, the at least one processor executing: a receiving process of receiving, from the another terminal device, a result of aggregation of (i) information indicating a body temperature of a user and (ii) at least one of information relating to the user and information relating to a mobile terminal; a generating process of generating, on the basis of the result of the aggregation received by the receiving process, a report including at least a percentage of people who are suspected to have an infectious disease in a given area; and a transmitting process of transmitting, to a server, the report generated by the generating process.

Note that the terminal device may further include a memory. In the memory, a program causing the processor to execute the receiving process, the generating process, and the transmitting process may be stored. The program may be stored in a non-transitory, tangible storage medium capable of being read by a computer.

A terminal device including at least one processor, the at least one processor executing: a detecting process of detecting a body temperature of a pedestrian; an authentication process of detecting, on the basis of an image of a face of the pedestrian, a symptom suspected to be of an infectious disease; a generating process of generating information given by aggregation of (i) information indicating the body temperature of the pedestrian detected by the detecting process and (ii) the symptom suspected to be of the infectious disease detected by the authentication process; and a transmitting process of transmitting, to another terminal device, the information generated by the generating process.

Note that the terminal device may further include a memory. In the memory, a program causing the processor to execute the detecting process, the authentication process, the generating process, and the transmitting process may be stored. The program may be stored in a non-transitory, tangible storage medium capable of being read by a computer.

Supplementary Note 4

Some or all of the above embodiments can be described as below. Note, however, that the present invention is not limited to aspects described below.

Aspect A1

A terminal device includes: a communication means that communicates with a first terminal device including a detecting means that detects information relating to a physical condition of a pedestrian and with a second terminal device including an obtaining means that obtains information relating to a physical condition of the pedestrian from a mobile terminal of the pedestrian; a difficulty information obtaining means that obtains information relating to difficulty in obtaining physical condition information in a place around the first terminal device; a selecting means that selects one of the first terminal device and the second terminal device on a basis of the information relating to the difficulty in obtaining the physical condition information; and a physical condition information obtaining means that obtains, from the one of the first and second terminal devices selected by the selecting means, the information relating to the physical condition of the pedestrian.

According to the above configuration, information relating to a person who is suspected to have an infectious disease in a given area can be collected suitably according to the situation, such as the situation of an obstacle.

Measure A2

The terminal device described in aspect A1, the terminal device further including: an instruction means that gives, to the one of the first and second terminal devices selected by the selecting means, an instruction to obtain the information relating to the physical condition of the pedestrian.

According to the above configuration, the physical condition information can be collected suitably after the instruction is given to the terminal device selected by the selecting means.

Aspect A3

The terminal device described in aspect A1 or A2, wherein: the information relating to the physical condition of the pedestrian detected by the first terminal device and the information relating to the physical condition of the pedestrian obtained by the second terminal device each include information relating to a body temperature of the pedestrian.

According to the above configuration, the suitable physical condition information including the information relating to the body temperature of the pedestrian can be collected.

Aspect A4

The terminal device described in any one of aspects A1 to A3, wherein: the difficulty information obtaining means obtains, as the information relating to the difficulty in obtaining the physical condition information, information relating to a status of communication between a mobile terminal of a user and the second terminal device.

According to the above configuration, the information relating to the difficulty in obtaining the physical condition information can be obtained suitably.

Aspect A5

The terminal device described in any one of aspects A1 to A3, wherein: the difficulty information obtaining means obtains, as the information relating to the difficulty in obtaining the physical condition information, a difference between a total number of living bodies recognized, through biometric authentication, by the detecting means included in the first terminal device in a predetermined period and a total number of faces recognized by the detecting means included in the first terminal device in the predetermined period.

According to the above configuration, the information relating to the difficulty in obtaining the physical condition information can be obtained suitably.

Aspect A6

The terminal device described in any one of aspects A1 to A5, wherein: the obtaining means included in the second terminal device obtains, from the mobile terminal of the pedestrian through near field communication, the information relating to the physical condition of the pedestrian.

According to the above configuration, the physical condition information can be obtained suitably.

Aspect A7

An information processing system including: a communication means that communicates with a first terminal device including a detecting means that detects information relating to a physical condition of a pedestrian and with a second terminal device including an obtaining means that obtains information relating to a physical condition of the pedestrian from a mobile terminal of the pedestrian; a difficulty information obtaining means that obtains information relating to difficulty in obtaining physical condition information in a place around the first terminal device; a selecting means that selects one of the first terminal device and the second terminal device on a basis of the information relating to the difficulty in obtaining the physical condition information; and a physical condition information obtaining means that obtains, from the one of the first and second terminal devices selected by the selecting means, the information relating to the physical condition of the pedestrian.

Aspect A8

The information processing system described in aspect A7, further including: an instruction means that gives, to the one of the first and second terminal devices selected by the selecting means, an instruction to obtain the information relating to the physical condition of the pedestrian.

Aspect A9

The information processing system described in aspect A7 or A8, wherein: the information relating to the physical condition of the pedestrian detected by the first terminal device and the information relating to the physical condition of the pedestrian obtained by the second terminal device each include information relating to a body temperature of the pedestrian.

Aspect A10

The information processing system described in any one of aspects A7 to A9, wherein: the difficulty information obtaining means obtains, as the information relating to the difficulty in obtaining the physical condition information, information relating to a status of communication between a mobile terminal of a user and the second terminal device.

Aspect A11

The information processing system described in any one of aspects A7 to A9, wherein: the difficulty information obtaining means obtains, as the information relating to the difficulty in obtaining the physical condition information, a difference between a total number of living bodies recognized, through biometric authentication, by the detecting means included in the first terminal device in a predetermined period and a total number of faces recognized by the detecting means included in the first terminal device in the predetermined period.

Aspect A12

The information processing system described in any one of aspects A7 to A11, wherein: the obtaining means included in the second terminal device obtains, from the mobile terminal of the pedestrian through near field communication, the information relating to the physical condition of the pedestrian.

Aspect A13

An information processing method including: obtaining information relating to difficulty in obtaining physical condition information in a place around a first terminal device including a detecting means that detects information relating to a physical condition of a pedestrian; selecting, on a basis of the information relating to the difficulty in obtaining the physical condition information, one of the first terminal device and a second terminal device including an obtaining means that obtains information relating to a physical condition of the pedestrian from a mobile terminal of the pedestrian; and obtaining, from the one of the first and second terminal devices thus selected, the information relating to the physical condition of the pedestrian.

Aspect A14

The information processing method described in aspect A13, further including: giving, to the one of the first and second terminal devices thus selected, an instruction to obtain the information relating to the physical condition of the pedestrian.

Aspect A15

The information processing method described in aspect A13 or A14, wherein: the information relating to the physical condition of the pedestrian detected by the first terminal device and the information relating to the physical condition of the pedestrian obtained by the second terminal device each include information relating to a body temperature of the pedestrian.

Aspect A16

The information processing method described in any one of aspects A13 to A15, wherein: in the obtaining the information relating to the difficulty in obtaining the physical condition information, information relating to a status of communication between a mobile terminal of a user and the second terminal device is obtained as the information relating to the difficulty in obtaining the physical condition information.

Aspect A17

The information processing method described in any one of aspects A13 to A15, wherein: in the obtaining the information relating to the difficulty in obtaining the physical condition information, a difference between a total number of living bodies recognized, through biometric authentication, by the detecting means included in the first terminal device, in a predetermined period and a total number of faces recognized by the detecting means included in the first terminal device in the predetermined period is obtained as the information relating to the difficulty in obtaining the physical condition information.

Aspect A18

The information processing method described in any one of aspects A13 to A17, wherein: the obtaining means included in the second terminal device obtains, from the mobile terminal of the pedestrian through near field communication, the information relating to the physical condition of the pedestrian.

Supplementary Note 5

Further, some or all of the above embodiments can be expressed as below.

A terminal device including at least one processor, the at least one processor executing: obtaining information relating to difficulty in obtaining physical condition information in a place around a first terminal device including a detecting means that detects information relating to a physical condition of a pedestrian; selecting, on a basis of the information relating to the difficulty in obtaining the physical condition information, one of the first terminal device and a second terminal device including an obtaining means that obtains information relating to a physical condition of a pedestrian from a mobile terminal of the pedestrian; and obtaining, from the one of the first and second terminal devices thus selected, the information relating to the physical condition of the pedestrian.

Note that the terminal device may further include a memory. In the memory, a program causing the processor to execute each of the processes may be stored. The program may be stored in a non-transitory, tangible storage medium capable of being read by a computer.

REFERENCE SIGNS LIST

1: network system
10, 10*a*: mobile terminal
11, 111, 201: detecting section
12: manipulation detecting section
13, 13*a*: control section
14, 204: communication section
15: image-capturing section
16, 112, 202: authentication section
20: computer
21: processor
22: memory
23: internal bus
30: storage medium
100: terminal device A 101, 301: first communication section
102, 203: generating section
103, 303: second communication section
113, 302: aggregation section
114: content collecting section
115: analyzing section
200: terminal device B
300: terminal device C
400: server
500: central network
600: local network
P: program

What is claimed is:

1. A terminal device comprising at least one processor, the at least one processor executing:

a process of communicating with a first terminal device including a detecting section that detects information relating to a physical condition of a pedestrian and with a second terminal device including an obtaining section that obtains information relating to a physical condition of the pedestrian from a mobile terminal of the pedestrian;

a process of obtaining information relating to difficulty in obtaining physical condition information in a place around the first terminal device;

a process of selecting one of the first terminal device and the second terminal device on a basis of the information relating to the difficulty in obtaining the physical condition information; and a process of obtaining, from the one of the first and second terminal devices thus selected, the information relating to the physical condition of the pedestrian wherein:

in the process of obtaining the information relating to the difficulty in obtaining the physical condition information, the at least one processor obtains, as the information relating to the difficulty in obtaining the physical condition information, a difference between a total number of living bodies recognized, through biometric authentication, by the detecting section included in the first terminal device in a predetermined period and a total number of faces recognized by the detecting section included in the first terminal device in the predetermined period.

2. The terminal device according to claim 1, wherein:

the at least one processor executes a process of giving, to the one of the first and second terminal devices thus selected, an instruction to obtain the information relating to the physical condition of the pedestrian.

3. The terminal device according to claim 1, wherein:

the information relating to the physical condition of the pedestrian detected by the first terminal device and the information relating to the physical condition of the pedestrian obtained by the second terminal device each include information relating to a body temperature of the pedestrian.

4. The terminal device according to claim 1, wherein:

in the process of obtaining the information relating to the difficulty in obtaining the physical condition information, the at least one processor obtains, as the information relating to the difficulty in obtaining the physical condition information, information relating to a status of communication between a mobile terminal of a user and the second terminal device.

5. The terminal device according to claim 1, wherein:

the obtaining section included in the second terminal device obtains, from the mobile terminal of the pedestrian through near field communication, the information relating to the physical condition of the pedestrian.

6. An information processing system comprising at least one processor, the at least one processor executing:

a process of communicating with a first terminal device including a detecting section that detects information relating to a physical condition of a pedestrian and with a second terminal device including an obtaining section that obtains information relating to a physical condition of the pedestrian from a mobile terminal of the pedestrian;

a process of obtaining information relating to difficulty in obtaining physical condition information in a place around the first terminal device;

a process of selecting one of the first terminal device and the second terminal device on a basis of the information relating to the difficulty in obtaining the physical condition information; and a process of obtaining, from the one of the first and second terminal devices thus selected, the information relating to the physical condition of the pedestrian, wherein:

in the process of obtaining the information relating to the difficulty in obtaining the physical condition information, the at least one processor obtains, as the information relating to the difficulty in obtaining the physical condition information, a difference between a total number of living bodies recognized, through biometric authentication, by the detecting section included in the first terminal device in a predetermined period and a total number of faces recognized by the detecting section included in the first terminal device in the predetermined period.

7. The information processing system according to claim 6, wherein:

the at least one processor gives, to the one of the first and second terminal devices thus selected, an instruction to obtain the information relating to the physical condition of the pedestrian.

8. The information processing system according to claim 6, wherein:

the information relating to the physical condition of the pedestrian detected by the first terminal device and the information relating to the physical condition of the pedestrian obtained by the second terminal device each include information relating to a body temperature of the pedestrian.

9. The information processing system according to claim 6, wherein:

in the process of obtaining the information relating to the difficulty in obtaining the physical condition information, the at least one processor obtains, as the information relating to the difficulty in obtaining the physical condition information, information relating to a status of communication between a mobile terminal of a user and the second terminal device.

10. The information processing system according to claim 6, wherein:

the obtaining section included in the second terminal device obtains, from the mobile terminal of the pedestrian through near field communication, the information relating to the physical condition of the pedestrian.

11. An information processing method comprising:

obtaining information relating to difficulty in obtaining physical condition information in a place around a first terminal device including a detecting section that detects information relating to a physical condition of a pedestrian;

selecting, on a basis of the information relating to the difficulty in obtaining the physical condition information, one of the first terminal device and a second terminal device including an obtaining section that obtains information relating to a physical condition of the pedestrian from a mobile terminal of the pedestrian; and obtaining, from the one of the first and second terminal devices thus selected, the information relating to the physical condition of the pedestrian, wherein, in the obtaining the information relating to the difficulty in obtaining the physical condition information, a difference between a total number of living bodies recognized, through biometric authentication, by the detecting section included in the first terminal device in a predetermined period and a total number of faces recognized by the detecting section included in the first terminal device in the predetermined period is obtained as the information relating to the difficulty in obtaining the physical condition information.

12. The information processing method according to claim 11, further comprising:

giving, to the one of the first and second terminal devices thus selected, an instruction to obtain the information relating to the physical condition of the pedestrian.

13. The information processing method according to claim 11, wherein:

the information relating to the physical condition of the pedestrian detected by the first terminal device and the information relating to the physical condition of the pedestrian obtained by the second terminal device each include information relating to a body temperature of the pedestrian.

14. The information processing method according to claim 11, in the obtaining the information relating to the difficulty in obtaining the physical condition information, information relating to a status of communication between a mobile terminal of a user and the second terminal device is obtained as the information relating to the difficulty in obtaining the physical condition information.

15. The information processing method according to claim 11, wherein:

the obtaining section included in the second terminal device obtains, from the mobile terminal of the pedestrian through near field communication, the information relating to the physical condition of the pedestrian.

* * * * *